US012564312B2

(12) United States Patent
Tilson et al.

(10) Patent No.: US 12,564,312 B2
(45) Date of Patent: Mar. 3, 2026

(54) MANAGING AND MANIPULATING A LONG LENGTH ROBOTIC ENDOSCOPE

(71) Applicant: Neptune Medical Inc., Burlingame, CA (US)

(72) Inventors: Alexander Q. Tilson, Burlingame, CA (US); Stephan T. Hoffmann, Danville, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 18/858,743

(22) PCT Filed: Apr. 18, 2023

(86) PCT No.: PCT/US2023/065910

§ 371 (c)(1),
(2) Date: Oct. 21, 2024

(87) PCT Pub. No.: WO2023/205655

PCT Pub. Date: Oct. 26, 2023

(65) Prior Publication Data

US 2025/0107697 A1      Apr. 3, 2025

Related U.S. Application Data

(60) Provisional application No. 63/332,686, filed on Apr. 19, 2022.

(51) Int. Cl.
*A61B 1/00*      (2006.01)
(52) U.S. Cl.
CPC ........ *A61B 1/00149* (2013.01); *A61B 1/0016* (2013.01)

(58) Field of Classification Search
CPC .......... A61B 2034/301; A61B 2034/305–306; A61B 1/0125; A61B 1/00147; A61B 1/00149; A61B 1/00154
See application file for complete search history.

(56) References Cited

U.S. PATENT DOCUMENTS 2,268,321 A      12/1941  Flynn
2,767,705 A      10/1956  Moore
(Continued)

FOREIGN PATENT DOCUMENTS

AU        2013207571 B2      8/2013
CN        2613655 Y          4/2004
(Continued)

OTHER PUBLICATIONS

Dow, Dow white paper: Can you estimate modulus from durometer hardness for silicones: Yes, but you only roughly and you must choose your modulus carefully!; 5 pages; retrieved from the internet (https://www.dow.com/content/dam/dcc/documents/en-us/tech-art/11/11-37/11-3716-01-durometer-hardness-for-silicones.pdf) on Jan. 18, 2023.

(Continued)

*Primary Examiner* — Michael J Carey
*Assistant Examiner* — Timothy Tuan Luu
(74) *Attorney, Agent, or Firm* — Shay Glenn LLP

(57)      ABSTRACT
Apparatuses and methods for storing and dispensing elongate, flexible, medical instruments, such as endoscopes, may be configured for rotary storage and dispensing, which provides substantial advantages in space management. In particular, described herein are systems for storing and dispensing a robotic scope that include a rotatable frame to which a robotic scope (e.g., endoscope, including a nested system) may be coupled for dispensing.

29 Claims, 28 Drawing Sheets

(56)                    References Cited

U.S. PATENT DOCUMENTS

| | | | |
|---|---|---|---|
| 3,466,220 A | 9/1969 | Allinikov et al. | |
| 3,859,986 A | 1/1975 | Okada et al. | |
| 3,998,216 A | 12/1976 | Hosono | |
| 4,066,071 A | 1/1978 | Nagel | |
| 4,141,364 A | 2/1979 | Schultze | |
| 4,151,800 A | 5/1979 | Dotts et al. | |
| 4,160,451 A * | 7/1979 | Chittenden ........ A61M 25/0113 | |
| | | | 242/405 |
| 4,176,662 A | 12/1979 | Frazer | |
| 4,425,919 A | 1/1984 | Alston, Jr. | |
| 4,551,140 A | 11/1985 | Shinohara | |
| 4,690,131 A | 9/1987 | Lyddy, Jr. et al. | |
| 4,696,544 A | 9/1987 | Costella | |
| 4,717,379 A | 1/1988 | Ekholmer | |
| 4,794,412 A | 12/1988 | Casey et al. | |
| 4,794,912 A | 1/1989 | Lia | |
| 4,815,450 A | 3/1989 | Patel | |
| 4,817,613 A | 4/1989 | Jaraczewski et al. | |
| 4,890,602 A | 1/1990 | Hake | |
| 4,893,613 A | 1/1990 | Hake | |
| 4,913,369 A | 4/1990 | Lia et al. | |
| 4,959,058 A | 9/1990 | Michelson | |
| 4,961,738 A | 10/1990 | Mackin | |
| 4,967,732 A | 11/1990 | Inoue | |
| 5,018,436 A | 5/1991 | Evangelista et al. | |
| 5,019,121 A | 5/1991 | Krauter | |
| 5,037,386 A | 8/1991 | Marcus et al. | |
| 5,037,404 A | 8/1991 | Gold et al. | |
| 5,050,585 A | 9/1991 | Takahashi | |
| 5,105,819 A | 4/1992 | Wollschlager et al. | |
| 5,123,421 A | 6/1992 | Sinofsky | |
| 5,125,143 A | 6/1992 | Takahashi | |
| 5,174,276 A | 12/1992 | Crockard | |
| 5,188,595 A | 2/1993 | Jacob | |
| 5,193,525 A | 3/1993 | Silverstein et al. | |
| 5,201,908 A | 4/1993 | Jones | |
| 5,251,611 A | 10/1993 | Zehel et al. | |
| 5,337,733 A | 8/1994 | Bauerfeind et al. | |
| 5,360,440 A | 11/1994 | Andersen | |
| 5,447,148 A | 9/1995 | Oneda et al. | |
| 5,496,292 A | 3/1996 | Burnham | |
| 5,531,685 A | 7/1996 | Hemmer et al. | |
| 5,531,719 A | 7/1996 | Takahashi | |
| 5,577,992 A | 11/1996 | Chiba et al. | |
| 5,601,588 A | 2/1997 | Tonomura et al. | |
| 5,603,991 A | 2/1997 | Kupiecki et al. | |
| 5,607,435 A | 3/1997 | Sachdeva et al. | |
| 5,624,381 A | 4/1997 | Kieturakis | |
| 5,632,734 A | 5/1997 | Galel et al. | |
| 5,637,075 A | 6/1997 | Kikawada | |
| 5,662,587 A | 9/1997 | Grundfest et al. | |
| 5,662,621 A | 9/1997 | Lafontaine | |
| 5,746,692 A | 5/1998 | Bacich et al. | |
| 5,749,828 A | 5/1998 | Solomon et al. | |
| 5,759,151 A | 6/1998 | Sturges | |
| 5,779,624 A | 7/1998 | Chang | |
| 5,782,811 A | 7/1998 | Samson et al. | |
| 5,823,961 A | 10/1998 | Fields et al. | |
| 5,882,347 A | 3/1999 | Mouris Laan et al. | |
| 5,891,112 A | 4/1999 | Samson | |
| 5,891,114 A | 4/1999 | Chin et al. | |
| 5,906,591 A | 5/1999 | Dario et al. | |
| 5,916,145 A | 6/1999 | Chu et al. | |
| 5,916,147 A | 6/1999 | Boury | |
| 5,951,539 A | 9/1999 | Nita et al. | |
| 5,976,074 A | 11/1999 | Moriyama | |
| 6,090,099 A | 7/2000 | Samson et al. | |
| 6,159,187 A | 12/2000 | Park et al. | |
| 6,162,171 A | 12/2000 | Ng et al. | |
| 6,165,123 A | 12/2000 | Thompson | |
| 6,179,776 B1 | 1/2001 | Adams et al. | |
| 6,190,357 B1 | 2/2001 | Ferrari et al. | |
| 6,217,565 B1 | 4/2001 | Cohen | |
| 6,296,644 B1 | 10/2001 | Surat et al. | |
| 6,309,346 B1 | 10/2001 | Farhadi | |
| 6,352,503 B1 | 3/2002 | Matsu et al. | |
| 6,364,878 B1 | 4/2002 | Hall | |
| 6,368,315 B1 | 4/2002 | Gillis et al. | |
| 6,468,203 B2 | 10/2002 | Belson | |
| 6,485,409 B1 | 11/2002 | Voloshin et al. | |
| 6,503,225 B1 | 1/2003 | Kirsch et al. | |
| 6,517,477 B1 | 2/2003 | Wendlandt | |
| 6,547,724 B1 | 4/2003 | Soble et al. | |
| 6,572,538 B2 | 6/2003 | Takase | |
| 6,572,590 B1 | 6/2003 | Stevens et al. | |
| 6,579,277 B1 | 6/2003 | Rabiner et al. | |
| 6,610,007 B2 | 8/2003 | Belson et al. | |
| 6,612,982 B1 | 9/2003 | Ouchi | |
| 6,616,628 B2 | 9/2003 | Hayzelden | |
| 6,620,126 B2 | 9/2003 | Unsworth et al. | |
| 6,623,424 B2 | 9/2003 | Hayakawa et al. | |
| 6,712,832 B2 | 3/2004 | Shah | |
| 6,726,677 B1 | 4/2004 | Flaherty et al. | |
| 6,730,020 B2 | 5/2004 | Peng et al. | |
| 6,780,151 B2 | 8/2004 | Grabover et al. | |
| 6,783,491 B2 | 8/2004 | Saadat et al. | |
| 6,790,173 B2 | 9/2004 | Saadat et al. | |
| 6,793,621 B2 | 9/2004 | Butler et al. | |
| 6,793,661 B2 | 9/2004 | Hamilton et al. | |
| 6,800,056 B2 | 10/2004 | Tartaglia et al. | |
| 6,869,393 B2 | 3/2005 | Butler | |
| 6,899,673 B2 | 5/2005 | Ogura et al. | |
| 6,911,004 B2 | 6/2005 | Kim et al. | |
| 6,923,754 B2 | 8/2005 | Lubock | |
| 6,960,162 B2 | 11/2005 | Saadat et al. | |
| 6,974,411 B2 | 12/2005 | Belson | |
| 6,984,203 B2 | 1/2006 | Tartaglia et al. | |
| 7,060,199 B2 | 6/2006 | Woydt et al. | |
| 7,172,552 B2 | 2/2007 | Wendlandt | |
| 7,214,230 B2 | 5/2007 | Brock et al. | |
| 7,273,469 B1 | 9/2007 | Chan et al. | |
| 7,288,101 B2 | 10/2007 | Deem et al. | |
| 7,291,127 B2 | 11/2007 | Eldenschink | |
| 7,354,427 B2 | 4/2008 | Fangrow | |
| 7,365,509 B2 | 4/2008 | Park et al. | |
| 7,438,712 B2 | 10/2008 | Chouinard | |
| 7,511,733 B2 | 3/2009 | Takizawa et al. | |
| 7,537,562 B2 | 5/2009 | Takano | |
| 7,559,916 B2 | 7/2009 | Smith et al. | |
| 7,591,782 B2 | 9/2009 | Fujikura | |
| 7,598,652 B2 | 10/2009 | Kornbluh et al. | |
| 7,658,738 B2 | 2/2010 | Nobis et al. | |
| 7,695,428 B2 | 4/2010 | Machida | |
| 7,736,323 B2 | 6/2010 | Von Weymarn-Scharli | |
| 7,749,196 B2 | 7/2010 | Osborne et al. | |
| 7,837,615 B2 | 11/2010 | Le et al. | |
| 7,850,725 B2 | 12/2010 | Vardi et al. | |
| 7,901,347 B2 | 3/2011 | Sekiguchi et al. | |
| 7,909,755 B2 | 3/2011 | Itol | |
| 7,918,819 B2 | 4/2011 | Karmarkar et al. | |
| 7,918,845 B2 | 4/2011 | Saadat et al. | |
| 7,931,661 B2 | 4/2011 | Saadat et al. | |
| 7,935,047 B2 | 5/2011 | Yoshida et al. | |
| 7,947,000 B2 | 5/2011 | Vargas et al. | |
| 7,957,790 B2 | 6/2011 | Kleen | |
| 7,970,455 B2 | 6/2011 | Zilberstein et al. | |
| 7,988,621 B2 | 8/2011 | Smith et al. | |
| 8,047,236 B2 | 11/2011 | Perry | |
| 8,075,476 B2 | 12/2011 | Vargas | |
| 8,092,374 B2 | 1/2012 | Smith et al. | |
| 8,109,953 B1 | 2/2012 | King, III et al. | |
| 8,123,739 B2 | 2/2012 | McQueen et al. | |
| 8,125,755 B2 | 2/2012 | Garcia et al. | |
| 8,192,422 B2 | 6/2012 | Zubiate et al. | |
| 8,206,287 B2 | 6/2012 | Matsuo | |
| 8,226,548 B2 | 7/2012 | Kucklick | |
| 8,241,299 B2 | 8/2012 | Hibner | |
| 8,246,575 B2 | 8/2012 | Viola | |
| 8,257,257 B2 | 9/2012 | Takizawa et al. | |
| 8,262,677 B2 | 9/2012 | Goto | |
| 8,298,161 B2 | 10/2012 | Vargas | |
| 8,313,014 B2 | 11/2012 | Bettuchi | |
| 8,361,090 B2 | 1/2013 | Belson | |
| 8,366,606 B2 | 2/2013 | Watanabe et al. | |

(56) References Cited

U.S. PATENT DOCUMENTS

| | | | |
|---|---|---|---|
| 8,388,519 B2 | 3/2013 | Garcia et al. |
| 8,439,825 B2 | 5/2013 | Sekiguchi |
| 8,460,179 B2 | 6/2013 | Ikeda et al. |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,777,844 B1 | 7/2014 | Sadanand |
| 8,920,369 B2 | 12/2014 | Salahleh et al. |
| 8,969,639 B2 | 3/2015 | Xu et al. |
| 8,992,420 B2 | 3/2015 | Maahs et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,282,993 B1 | 3/2016 | Cohen et al. |
| 9,295,511 B2 | 3/2016 | Smith et al. |
| 9,333,287 B2 | 5/2016 | Nitsan et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 9,993,142 B2 | 6/2018 | Salman et al. |
| 10,092,291 B2 | 10/2018 | Voegele et al. |
| 10,307,042 B2 | 6/2019 | Lombardi |
| 10,463,495 B2 | 11/2019 | Rogers et al. |
| 10,625,413 B1 | 4/2020 | McPherson |
| 11,006,975 B1 | 5/2021 | Cohen et al. |
| 11,020,214 B2 | 6/2021 | Gupta et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 11,554,248 B1 | 1/2023 | Tilson et al. |
| 11,724,065 B2 | 8/2023 | Tilson et al. |
| 11,744,443 B2 | 9/2023 | Lopez et al. |
| 11,793,392 B2 | 10/2023 | Tilson et al. |
| 11,937,778 B2 | 3/2024 | Tilson et al. |
| 11,944,277 B2 | 4/2024 | Tilson et al. |
| 12,059,128 B2 | 8/2024 | Tilson et al. |
| 12,082,776 B2 | 9/2024 | Tilson et al. |
| 12,102,289 B2 | 10/2024 | Tilson et al. |
| 12,121,677 B2 | 10/2024 | Gomes et al. |
| 12,193,637 B2 | 1/2025 | Tilson et al. |
| 2001/0041881 A1 | 11/2001 | Sarge et al. |
| 2002/0049423 A1 | 4/2002 | Howell et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0035048 A1 | 2/2003 | Shipp |

| | | | |
|---|---|---|---|
| 2003/0036748 A1 | 2/2003 | Cooper et al. |
| 2003/0083546 A1 | 5/2003 | Butler et al. |
| 2003/0122374 A1 | 7/2003 | Ouchi et al. |
| 2003/0153866 A1 | 8/2003 | Long et al. |
| 2003/0208220 A1 | 11/2003 | Worley et al. |
| 2003/0216681 A1 | 11/2003 | Zhang et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0242958 A1* | 12/2004 | Fujikawa ........... G02B 23/2476 600/102 |
| 2004/0243227 A1 | 12/2004 | Starksen et al. |
| 2004/0260236 A1 | 12/2004 | Manning et al. |
| 2005/0004523 A1 | 1/2005 | Osborne et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0154258 A1 | 7/2005 | Tartaglia et al. |
| 2005/0165275 A1 | 7/2005 | Von Felten et al. |
| 2005/0165366 A1 | 7/2005 | Brustad et al. |
| 2005/0203340 A1 | 9/2005 | Butler et al. |
| 2005/0261581 A1 | 11/2005 | Hughes et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0063973 A1 | 3/2006 | Makower et al. |
| 2006/0129130 A1 | 6/2006 | Tal et al. |
| 2006/0178560 A1 | 8/2006 | Saadat et al. |
| 2006/0192465 A1 | 8/2006 | Kornbluh et al. |
| 2006/0199999 A1 | 9/2006 | Ikeda et al. |
| 2006/0235457 A1 | 10/2006 | Belson |
| 2006/0235458 A1 | 10/2006 | Belson |
| 2006/0258906 A1 | 11/2006 | Binmoeller |
| 2006/0264707 A1 | 11/2006 | Kinney |
| 2006/0264821 A1 | 11/2006 | Vo et al. |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0135803 A1 | 6/2007 | Belson |
| 2007/0156018 A1 | 7/2007 | Krauter et al. |
| 2007/0219411 A1 | 9/2007 | Dejima et al. |
| 2007/0239252 A1 | 10/2007 | Hopkins et al. |
| 2007/0250113 A1 | 10/2007 | Hegeman et al. |
| 2007/0250149 A1 | 10/2007 | Oepen et al. |
| 2007/0255101 A1 | 11/2007 | Bar Or |
| 2007/0260121 A1 | 11/2007 | Bakos et al. |
| 2007/0282358 A1 | 12/2007 | Remiszewski et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahleh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0249362 A1 | 10/2008 | Jiang et al. |
| 2008/0262300 A1 | 10/2008 | Ewers et al. |
| 2008/0275299 A1 | 11/2008 | Park |
| 2009/0023983 A1 | 1/2009 | Stefanchik |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0062872 A1 | 3/2009 | Chin et al. |
| 2009/0104250 A1 | 4/2009 | Boyden et al. |
| 2009/0112063 A1 | 4/2009 | Bakos et al. |

(56)                    References Cited

U.S. PATENT DOCUMENTS

| | | |
|---|---|---|
| 2009/0112064 A1 | 4/2009 | Levey et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0248041 A1 | 10/2009 | Williams et al. |
| 2009/0259200 A1 | 10/2009 | Lampropoulos |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0010504 A1 | 1/2010 | Simaan et al. |
| 2010/0016663 A1 | 1/2010 | Maisch et al. |
| 2010/0036363 A1 | 2/2010 | Watanabe et al. |
| 2010/0069712 A1 | 3/2010 | Yamaya |
| 2010/0069716 A1 | 3/2010 | Chin et al. |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0185172 A1 | 7/2010 | Fabro |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1 | 2/2011 | Vazales et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0087070 A1 | 4/2011 | Tilson et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0288553 A1 | 11/2011 | Jansen et al. |
| 2011/0301414 A1 | 12/2011 | Hotto et al. |
| 2011/0306950 A1 | 12/2011 | Cucin |
| 2011/0319714 A1 | 12/2011 | Roelle et al. |
| 2012/0004676 A1 | 1/2012 | Vargas |
| 2012/0022329 A1 | 1/2012 | Wagh et al. |
| 2012/0041291 A1 | 2/2012 | Ferren et al. |
| 2012/0095448 A1 | 4/2012 | Kaji |
| 2012/0095548 A1 | 4/2012 | Gregorich et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0209292 A1 | 8/2012 | Devengenzo et al. |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0274553 A1 | 10/2013 | Piskun |
| 2013/0304179 A1 | 11/2013 | Bialas et al. |
| 2013/0333472 A1 | 12/2013 | Georgeson |
| 2013/0338440 A1 | 12/2013 | Sinai et al. |
| 2014/0005683 A1 | 1/2014 | Stand et al. |
| 2014/0073853 A1 | 3/2014 | Swisher et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0243796 A1 | 8/2014 | Tegg et al. |
| 2014/0243873 A1 | 8/2014 | Franklin |
| 2014/0275860 A1 | 9/2014 | Rottenberg et al. |
| 2014/0276601 A1 | 9/2014 | Edward |
| 2014/0276642 A1 | 9/2014 | Cully et al. |
| 2014/0309587 A1 | 10/2014 | Kim et al. |
| 2014/0343358 A1 | 11/2014 | Hameed et al. |
| 2014/0371718 A1 | 12/2014 | Alvarez et al. |
| 2014/0371764 A1 | 12/2014 | Oyola et al. |
| 2015/0018616 A1 | 1/2015 | Kumoyama |
| 2015/0038919 A1 | 2/2015 | Bramwell et al. |
| 2015/0073216 A1 | 3/2015 | Papay |
| 2015/0073342 A1* | 3/2015 | Pacheco ............ A61M 25/0113 604/95.04 |
| 2015/0073409 A1 | 3/2015 | Watson et al. |
| 2015/0094656 A1 | 4/2015 | Salahieh et al. |
| 2015/0119640 A1 | 4/2015 | Reydel |
| 2015/0126814 A1 | 5/2015 | Mesallum et al. |
| 2015/0133729 A1 | 5/2015 | Reydel |
| 2015/0142013 A1 | 5/2015 | Tanner et al. |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1 | 8/2015 | Wittenberger et al. |
| 2015/0276097 A1 | 10/2015 | Carlson et al. |
| 2015/0335387 A1 | 11/2015 | Atzinger et al. |
| 2015/0342608 A1 | 12/2015 | Hernandez |
| 2015/0369325 A1 | 12/2015 | Bureau et al. |
| 2016/0007832 A1 | 1/2016 | Shimada |
| 2016/0015259 A1 | 1/2016 | Mody et al. |
| 2016/0038002 A1 | 2/2016 | Peters et al. |
| 2016/0058268 A1 | 3/2016 | Salman et al. |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1 | 7/2016 | Choi et al. |
| 2016/0206425 A1 | 7/2016 | Madrid et al. |
| 2016/0270870 A1 | 9/2016 | Kowshik |
| 2016/0279388 A1* | 9/2016 | Barrish ............ A61M 25/1036 |
| 2016/0287059 A1 | 10/2016 | Ha et al. |
| 2016/0324412 A1 | 11/2016 | Hassidov et al. |
| 2017/0023154 A1 | 1/2017 | Jaeker et al. |
| 2017/0156567 A1 | 6/2017 | Kaneko |
| 2017/0157363 A1 | 6/2017 | Barrish et al. |
| 2017/0312920 A1 | 11/2017 | Yip et al. |
| 2017/0333681 A1 | 11/2017 | Di Caprio et al. |
| 2017/0340862 A1 | 11/2017 | Calabrese et al. |
| 2017/0360281 A1 | 12/2017 | Ponsky |
| 2018/0015257 A1 | 1/2018 | Krolik et al. |
| 2018/0043134 A1 | 2/2018 | Alvarez et al. |
| 2018/0064366 A1 | 3/2018 | Sweeney et al. |
| 2018/0085559 A1 | 3/2018 | Laby et al. |
| 2018/0132705 A1 | 5/2018 | Higuchi |
| 2018/0184885 A1 | 7/2018 | St. George |
| 2018/0249893 A1 | 9/2018 | Yeung et al. |
| 2018/0256876 A1 | 9/2018 | Furnish et al. |
| 2018/0263469 A1 | 9/2018 | Okaniwa et al. |
| 2018/0264239 A1 | 9/2018 | Piskun |
| 2018/0289925 A1 | 10/2018 | Palmer et al. |
| 2018/0326197 A1 | 11/2018 | McArthur et al. |
| 2018/0361116 A1 | 12/2018 | Quick et al. |
| 2018/0374603 A1 | 12/2018 | Greenwood |
| 2019/0046012 A1 | 2/2019 | Ikeda |
| 2019/0226447 A1 | 7/2019 | Stecher et al. |
| 2020/0022712 A1 | 1/2020 | Deville et al. |
| 2020/0030575 A1 | 1/2020 | Bogusky et al. |
| 2020/0100653 A1 | 4/2020 | Nakamura |
| 2020/0171276 A1 | 6/2020 | Onozuka |
| 2020/0178763 A1 | 6/2020 | Tilson et al. |
| 2020/0230808 A1 | 7/2020 | Simaan et al. |
| 2020/0237198 A1 | 7/2020 | Liu et al. |
| 2020/0315429 A1 | 10/2020 | Russo et al. |
| 2020/0315433 A1 | 10/2020 | Axon et al. |
| 2020/0383677 A1 | 12/2020 | Piligian et al. |
| 2020/0391002 A1 | 12/2020 | Hilton et al. |
| 2021/0000505 A1 | 1/2021 | Lenker et al. |
| 2021/0030260 A1 | 2/2021 | Julian et al. |
| 2021/0045626 A1 | 2/2021 | Hsu et al. |
| 2021/0114507 A1 | 4/2021 | Alexander et al. |
| 2021/0197684 A1 | 7/2021 | Graham et al. |
| 2021/0228973 A1 | 7/2021 | Conte |
| 2021/0323767 A1 | 10/2021 | Liu et al. |
| 2021/0330938 A1 | 10/2021 | Kendrick et al. |
| 2022/0323166 A1 | 10/2022 | Tilson et al. |

(56) References Cited

U.S. PATENT DOCUMENTS

| | | |
|---|---|---|
| 2022/0347430 A1 | 11/2022 | Pedersen |
| 2023/0017488 A1* | 1/2023 | Somasundaram ... A61B 1/0056 |
| 2023/0034024 A1 | 2/2023 | Cope et al. |
| 2023/0070264 A1 | 3/2023 | Leuthardt et al. |
| 2023/0121021 A1 | 4/2023 | Sinay et al. |
| 2023/0138203 A1 | 5/2023 | Bazdanes et al. |
| 2023/0210351 A1 | 7/2023 | Scheeff et al. |
| 2023/0338702 A1 | 10/2023 | Tilson et al. |
| 2023/0346204 A1 | 11/2023 | Tilson et al. |
| 2023/0346205 A1 | 11/2023 | Tilson et al. |
| 2023/0346399 A1 | 11/2023 | Schaller et al. |
| 2023/0353879 A1 | 11/2023 | Nishide et al. |
| 2023/0380662 A1 | 11/2023 | Slawinski et al. |
| 2023/0404486 A1 | 12/2023 | Carreel et al. |
| 2023/0404701 A1 | 12/2023 | Romo et al. |
| 2024/0016638 A1 | 1/2024 | McGowan et al. |
| 2024/0016639 A1 | 1/2024 | McGowan et al. |
| 2024/0024640 A1 | 1/2024 | Gomes et al. |
| 2024/0082557 A1 | 3/2024 | Tilson et al. |
| 2024/0090744 A1 | 3/2024 | Lopez et al. |
| 2024/0165833 A1 | 5/2024 | Tanner et al. |
| 2024/0293003 A1 | 9/2024 | Tilson et al. |
| 2024/0339112 A1 | 10/2024 | Rabinovich et al. |
| 2024/0350000 A1 | 10/2024 | Tilson et al. |
| 2024/0350768 A1 | 10/2024 | Tilson et al. |
| 2024/0408351 A1 | 12/2024 | Tilson et al. |
| 2024/0408352 A1 | 12/2024 | Tilson et al. |
| 2025/0090801 A1 | 3/2025 | Zayed et al. |
| 2025/0134352 A1 | 5/2025 | Tilson et al. |
| 2025/0169678 A1 | 5/2025 | Tilson et al. |
| 2025/0194904 A1 | 6/2025 | Tilson et al. |

FOREIGN PATENT DOCUMENTS

| | | |
|---|---|---|
| CN | 1706349 A | 12/2005 |
| CN | 1732855 A | 2/2006 |
| CN | 1764800 A | 4/2006 |
| CN | 1806770 A | 7/2006 |
| CN | 1861011 A | 11/2006 |
| CN | 101119765 A | 2/2008 |
| CN | 101129255 A | 2/2008 |
| CN | 101888872 A | 11/2010 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105813536 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 106823102 A | 6/2017 |
| CN | 107296584 A | 10/2017 |
| CN | 107697631 A | 2/2018 |
| CN | 110077771 A | 8/2019 |
| CN | 212558299 U | 2/2021 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| EP | 2604175 B1 | 11/2019 |
| GB | 2482355 A | 10/2010 |
| GB | 2497544 A | 6/2013 |
| JP | S6289014 A | 4/1987 |
| JP | H05220102 A | 8/1993 |
| JP | H05293077 A | 11/1993 |
| JP | H0644503 U | 6/1994 |
| JP | H06335531 A | 12/1994 |
| JP | 2002125921 A | 5/2002 |
| JP | 2003501197 A | 1/2003 |
| JP | 2003508133 A | 3/2003 |
| JP | 2005152300 A | 6/2005 |
| JP | 2005323778 A | 11/2005 |
| JP | 2006068449 A | 3/2006 |
| JP | 03965108 B2 | 8/2007 |
| JP | 2009506839 A | 2/2009 |
| JP | 2009507617 A | 2/2009 |
| JP | 2009061173 A | 3/2009 |
| JP | 2010000360 A | 1/2010 |
| JP | 2011194126 A | 10/2011 |
| JP | 2012183232 A | 9/2012 |
| JP | 2013514150 A | 4/2013 |
| JP | 2013176465 A | 9/2013 |
| JP | 2014124475 A | 7/2014 |
| JP | 2015525609 A | 9/2015 |
| JP | 2018500054 A | 1/2018 |
| JP | 2018514350 A | 6/2018 |
| JP | 2018525197 A | 9/2018 |
| JP | 2018537229 A | 12/2018 |
| JP | 6829351 B1 | 2/2021 |
| JP | 2021175686 A | 11/2021 |
| KR | 10-2015-0131502 A | 11/2015 |
| KR | 20180053852 A | 5/2018 |
| KR | 101908933 B1 | 10/2018 |
| WO | WO97/43941 A1 | 11/1997 |
| WO | WO99/053827 A1 | 10/1999 |
| WO | WO03/013348 A1 | 2/2003 |
| WO | WO2005/110199 A1 | 11/2005 |
| WO | WO2005/110200 A1 | 11/2005 |
| WO | WO2007/035931 A2 | 3/2007 |
| WO | WO2008/041809 A1 | 4/2008 |
| WO | WO2008/122969 A1 | 10/2008 |
| WO | WO2008/122997 A1 | 10/2008 |
| WO | WO2009/154192 A1 | 12/2009 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2013/132992 A1 | 9/2013 |
| WO | WO2016/034598 A1 | 3/2016 |
| WO | WO2016/190324 A1 | 12/2016 |
| WO | WO2017/041052 A1 | 3/2017 |
| WO | WO2018/035452 A1 | 8/2017 |
| WO | WO2019/054867 A1 | 3/2019 |
| WO | WO2019/160865 A1 | 8/2019 |
| WO | WO2020/018934 A1 | 1/2020 |
| WO | WO2020/214221 A1 | 10/2020 |
| WO | WO2020/237426 A1 | 12/2020 |
| WO | WO2021/202336 A1 | 10/2021 |
| WO | WO2021/242884 A1 | 12/2021 |
| WO | WO2022/051682 A1 | 3/2022 |
| WO | WO2022/087093 A1 | 4/2022 |
| WO | WO2022/146939 A1 | 7/2022 |
| WO | WO2022/159861 A1 | 7/2022 |
| WO | WO2023/122667 A1 | 6/2023 |
| WO | WO2023/122767 A2 | 6/2023 |
| WO | WO2023/133403 A1 | 7/2023 |
| WO | WO2023/154743 A2 | 8/2023 |
| WO | WO2023/212641 A2 | 11/2023 |
| WO | WO2023/225520 A2 | 11/2023 |
| WO | WO2013/184192 A2 | 12/2023 |
| WO | WO2024/030975 A2 | 2/2024 |

OTHER PUBLICATIONS

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

(56)                References Cited

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. On Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Mayinger et al.; Disposable-sheath, flexible gastroscope system versus standard gastroscopes: a prospective, randomized trial; Gastrointestinal Endoscopy; 50(4); pp. 461-467, Oct. 1999.

Mayinger et al.; Disposable protection for flexible gastroenterologic endoscopy: prospective comparative evaluation of a new gastroscopy system (Endosheath) compared to the standard fiberglass gastroscope; (English Abstract Only); Zeitschrift Fur Gastrenterologia; 36(6); pp. 501-507; Jun. 1998 (Eng Abs only).

Ofstead et al.; A systematic review of disposable sheath use during flexible endoscopy; AORN Journal; 109(6); pp. 757-771; Jun. 2019.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Lopez et al.; U.S. Appl. No. 18/723,414 entitled "Methods and apparatuses for reducing curvature of a colon," filed Jun. 21, 2024.

Gomes et al.; U.S. Appl. No. 18/723,413 entitled "Obturator with stiff distal cannula engagement region," filed Jun. 21, 2024.

Morris et al.; U.S. Appl. No. 18/727,032 entitled "Reconfigurable rigidizing structures," filed Jul. 5, 2024.

Tilson et al.; U.S. Appl. No. 18/780,429 entitled "Device for endoscopic advancement through the small intestine," filed Jul. 22, 2024.

Eisler et al.; U.S. Appl. No. 18/852,419 entitled "Rigidizing aspiration systems and methods," filed Sep. 27, 2024.

Gomes et al.; U.S. Appl. No. 18/837,186 entitled "Dynamically rigidizing composite medical structure," filed Aug. 8, 2024.

Witte et al.; U.S. Appl. No. 18/829,229 entitled "Pressure rigidization apparatuses and methods," filed Sep. 9, 2024.

Tilson et al.; U.S. Appl. No. 18/902,916 entitled "Methods of attaching a rigidizing sheath to an endoscope," filed Sep. 30, 2024.

Devengenzo et al.; U.S. Appl. No. 18/902,906 entitled "Telescoping robot," filed Sep. 30, 2024.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 18/908,776 entitled "Methods of attaching a rigidizing sheath to an endoscope," filed Oct. 7, 2024.

Tilson et al.; U.S. Appl. No. 19/100,929 entitled "Dynamic rigidization methods and apparatuses," filed Feb. 3, 2025.

Devengenzo et al.; U.S. Appl. No. 19/210,595 entitled "Telescoping robot," filed May 16, 2025.

Tilson et al.; U.S. Appl. No. 19/210,485 entitled "Methods of attaching a rigidizing sheath to an endoscope," filed May 16, 2025.

* cited by examiner

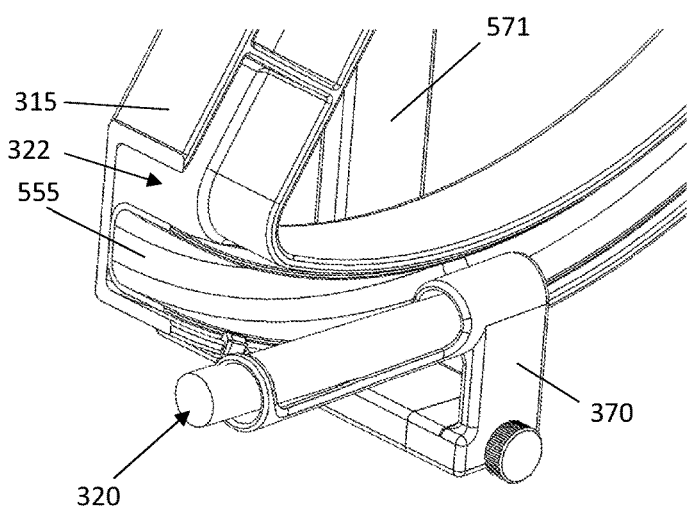
FIG. 5C
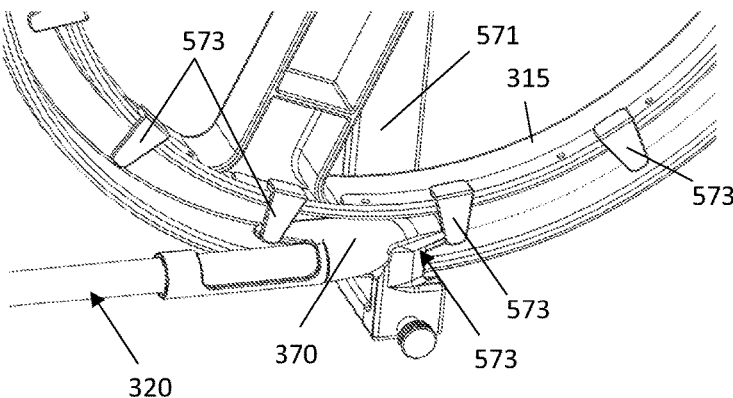
FIG. 5D
FIG. 5E

970

320

915

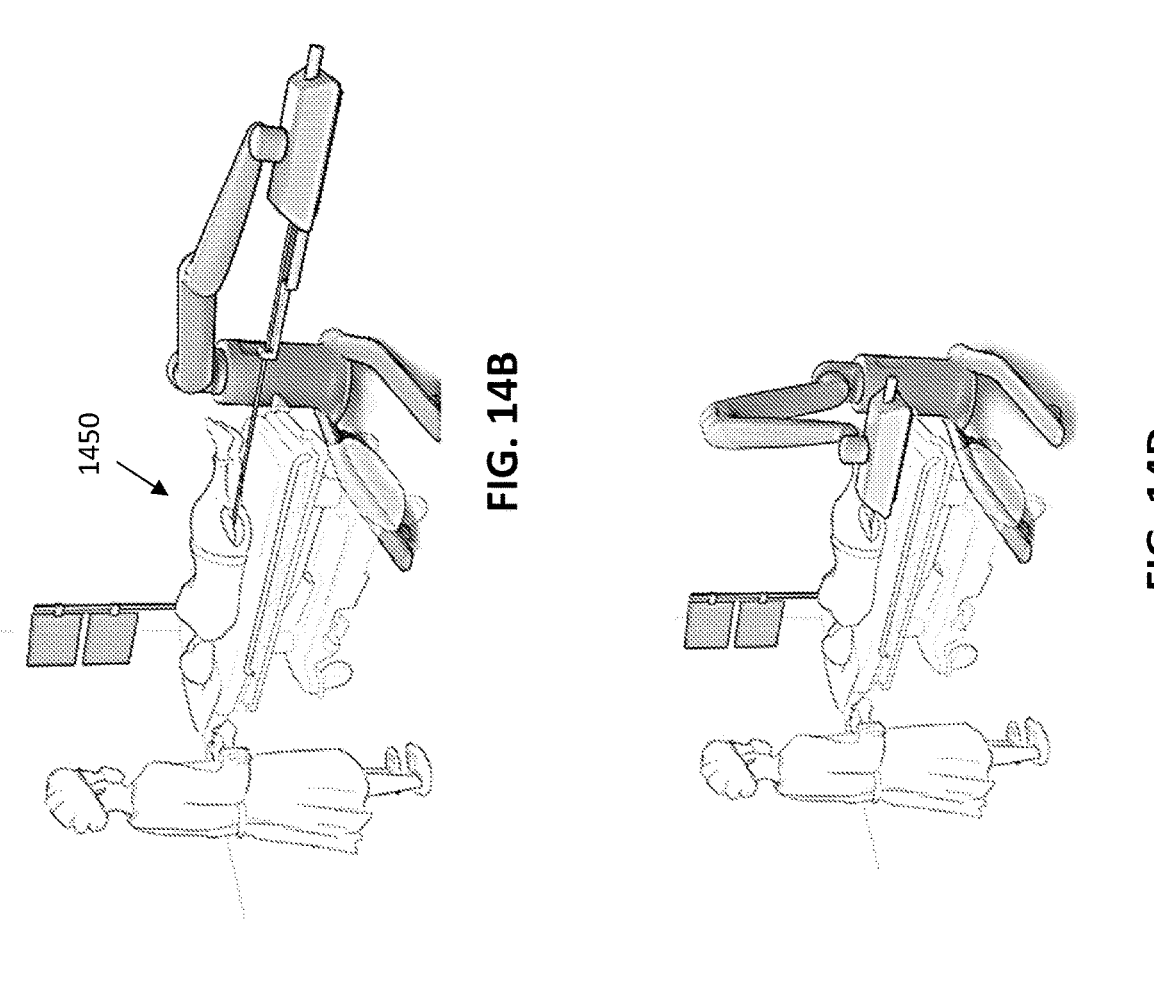
FIG. 14B
FIG. 14D
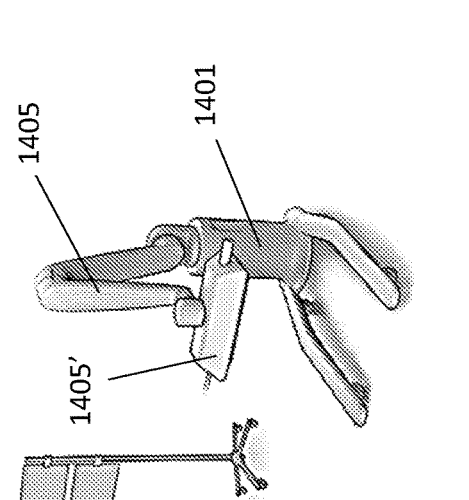
FIG. 14A
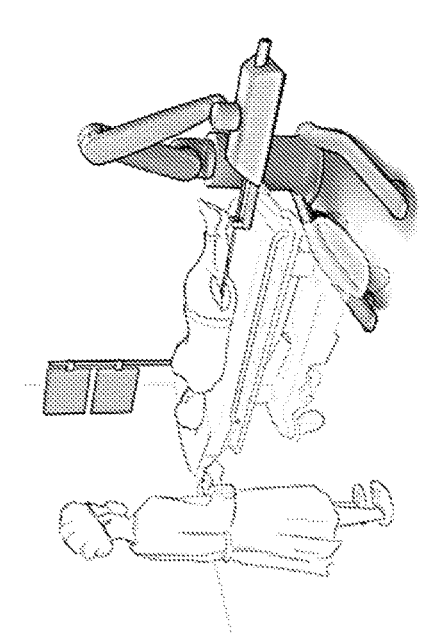
FIG. 14C

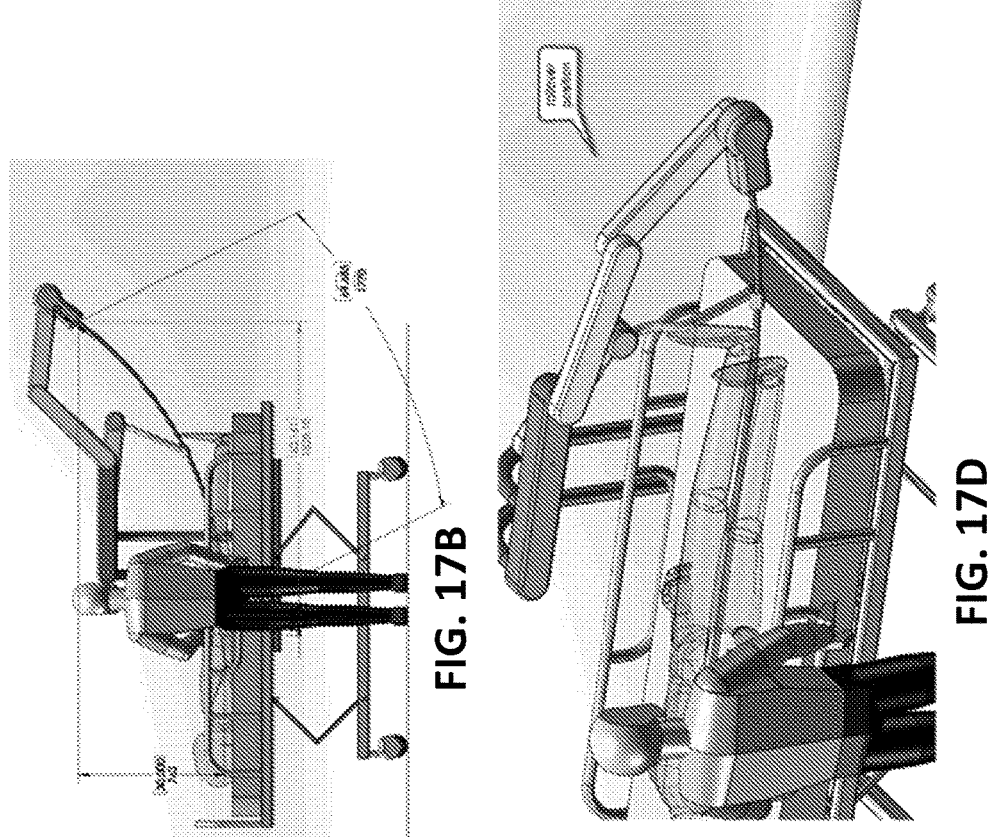
FIG. 17B
FIG. 17D
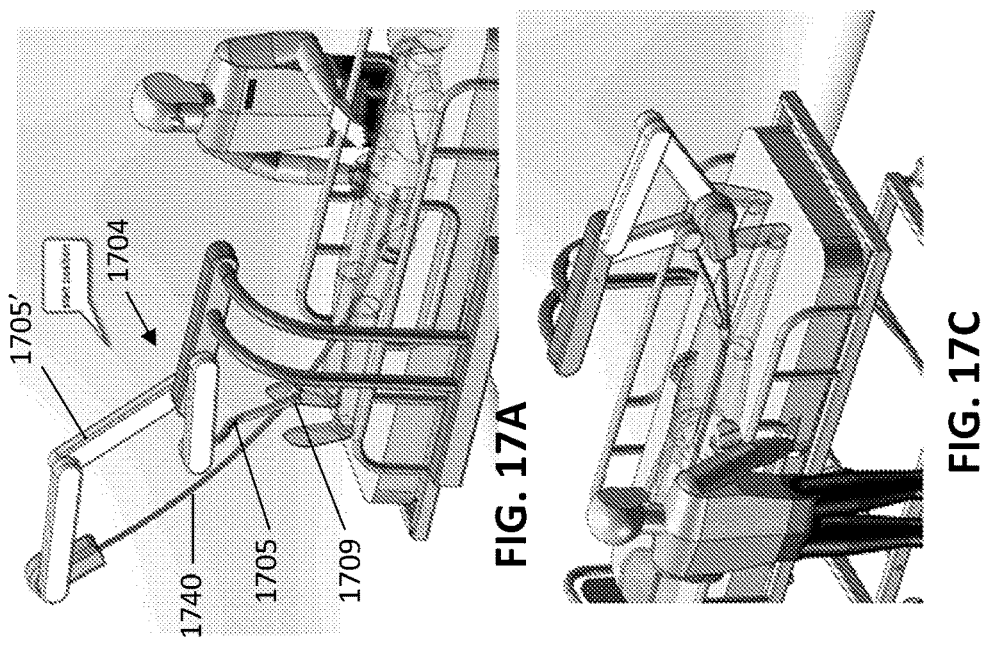
FIG. 17A
FIG. 17C

MANAGING AND MANIPULATING A LONG LENGTH ROBOTIC ENDOSCOPE

CLAIM OF PRIORITY

This patent application is a national phase application under 35 USC 371 of International Patent Application No. PCT/US2023/065910, titled "MANAGING AND MANIPULATING A LONG LENGTH ROBOTIC ENDO-SCOPE," filed on Apr. 18, 2023, now International Publication No. WO 2023/205655, which claims priority to U.S. provisional patent application No. 63/332,686, titled "MANAGING AND MANIPULATING A LONG LENGTH ROBOTIC ENDOSCOPE," filed on Apr. 19, 2022, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Medical procedures such as endoscopy may involve accessing and visualizing the inside of a patient's anatomy for diagnostic and/or therapeutic purposes. For example, gastroenterology, urology, and bronchoscopy involve medical procedures that allow a physician to examine patient lumens, such as the gastrointestinal tract, urology tract, vasculature, and airways. During these procedures, a flexible tool or instrument, typically referred to as an endoscope, overtube, catheter, or guidewire is inserted into the patient through an orifice (such as a natural orifice or an incision) and advanced towards a tissue site identified for subsequent diagnosis and/or treatment. The medical instrument can be controllable and articulable to facilitate navigation through the anatomy.

Management of these devices may be particularly challenging in already crowded operating rooms. Colonoscopes are just one example of a device, in this case an endoscope, that may be long and difficult to manage, particularly for robotic systems in which advancing/retracting and/or steering may be driven by a controller such as a robotic controller. Enteroscopes are used for navigation of the small intestine, and they may be even longer in length. Somewhat similar challenges exist for catheters, which are also longer length and flexible. Vascular catheters may advance into the neurovasculature, peripheral vasculature, pulmonary vasculature, and the cardiac and coronary vasculature. Guidewires may be used in the vasculature, usually in conjunction with catheters. Overtubes may be used with endoscopes. Overtubes may be used in conjunction with endoscopes, or an endoscope may be withdrawn such that only an overtube remains.

Although a large number of elongate, flexible, insertable tools (e.g., endoscopes, catheters, overtubes, guidewires, etc.) are used, or have been suggested for use, in medical procedures, storage and dispensing of such apparatuses becomes increasingly unwieldy as their length increases. Most shorter length robotic systems store the apparatus in a linear manner, but this approach becomes very limiting as length increases, such as with colonoscopes and enteroscopes. Another storage paradigm is simply to store the device drooped, limp, or on the table, all of which presents procedural limitations. Thus, there is a need for storage and dispensing methods and apparatuses that allow compact and efficient operation of elongate medical instruments, such as endoscopes, catheters, overtubes and guidewires.

SUMMARY OF THE DISCLOSURE

Described herein are apparatuses (e.g., systems, devices, etc.) and methods for storing, loading, dispensing or deploy-ment, driving (e.g., advancing/retracting, steering, etc.), and withdrawing one or more endoscopes, catheters, overtubes and/or guidewires, and in particular long-length endoscopes, including colonoscopes and enteroscopes. The methods and apparatuses described herein may address the challenges of storing, loading, dispensing or deployment, driving, and withdrawing and/or otherwise operating such elongate medical instruments. In particular, described herein are compact apparatuses for storing and dispensing flexible elongate medical instruments.

In general, these apparatuses may store the elongate medical instrument (e.g., endoscopes) in a compact, coiled configuration and may dispense the elongate medical instrument in a linear configuration. For example, these apparatuses may store the elongate medical instrument in a rotary configuration (e.g., at least partially coiled configuration), and may use a drive system, such as but not limited to a robotic system (e.g., a robotic arm systems) to apply a rotational motion to dispenses the elongate medical instrument into the body in a substantially linear orientation.

In general, the elongate medical instruments described herein may be referred to as robotic endoscopes or robotic scopes. These robotic scopes may include endoscopes, which may be actuated as described herein by the drive system, including robotic drive systems. Endoscopes may include colonoscopes, bronchoscope, colposcope, cystoscope, esophagoscope, gastroscope, laparoscope, thoracoscope, enteroscope, etc. In particular, the methods and apparatuses described herein may be particularly desirable for use with longer elongate medical instruments (e.g., having a length of greater than 0.7 m, 0.8 m, 0.9 m, 1 m, 1.2 m, 1.4 m, 1.6 m, 2.0 m, 2.1 m, 3 m, etc.).

These apparatuses may work well with endoscopes. These apparatuses may work particularly well with elongate medical instruments that include nested (i.e., two or more) components that may extend and retract relative to each other, such as telescoping elongate medical instruments. For example, a telescoping elongate medical instrument may include an inner robotic scope and an outer overtube. For example, a telescoping elongate medical instrument may include an inner robotic scope and an outer robotic scope. Either or both the inner and outer robotic scopes may be steerable, e.g., may include one or more steering member (e.g., steering tendons, etc.) that may mate with a steering interface on the apparatus. Either or both of the inner and outer scopes may include vision systems. The drive system may include a steering interface for the robotic scope, and in some examples for either or both an inner and an outer member of the robotic scope. Because nested systems involve more elements and more DOF (Degrees of Freedom), their storage, loading, deployment, driving, and withdrawal and kinematic control is particularly challenging, and therefore a particularly good fit to robotics, as robotic systems can execute complex kinematic maneuvers in a more facile manner, including through the use of software, algorithms, sensors, and actuators.

The methods and apparatuses described herein may be particularly well suited for controlling rigidizing elongate medical instruments (i.e., Dynamic Rigidization™). Rigidizing elongate medical instruments may include, but are not limited to, elongate medical instruments that are rigidized by multiple methods. One method for rigidization is the application of pressure (e.g., positive pressure and/or negative pressure). For example, the apparatuses and methods described herein may be particularly well suited for telescoping rigidizing elongate medical instruments in which an outer member of the robotic scope is a rigidizable member that may be rigidized by the application of pressure, and an inner member is a rigidizable member that may be rigidized by the application of pressure. The inner and outer members may be controllably rigidized separately and/or independently (or in a coordinated manner) which may be integrated with the drive system (e.g., robotic drive system).

Any of these apparatuses may be configured with components that are single use ('disposable'), multiple or multi-use ('resposable'), sheathed, or a very large number of uses ('reusable'). These elements may be engineered to reduce cost and landfill. They may be engineered for lower effective per-case cost. They may be engineered for ease of use, ease of install, fast procedure set-up, and ease of removal. Any of these apparatuses may be configured to allow reuse of drive system and frame, and other components that are coupled to the drive system, and may include one or more disposable components such as trays, cartridges, or the like to allow use with multiple robotic scopes, which may include sterile versions or sterile boundaries or layers. In any of these examples the apparatus may be configured so that the reusable component (e.g., the drive system, tray, pivot arm, etc.) may be configured to be kept separate from the sterile field, e.g., by the use of a drape or cover. Thus, also described herein are trays and/or cartridges that may engage with the apparatuses coupled to or including the drive systems described herein.

For example, described herein are apparatuses (e.g., systems and/or devices) for storing and dispensing a robotic scope, the system comprising: a cart, a robotic arm, a frame; a rotation mount at a rotational center of the frame, wherein the rotation mount is configured to couple to a drive system for rotation of the frame about a rotational center; a securement extending radially around the frame in an arc, wherein the securement is configured to hold the robotic scope; and an exit guide configured to mount to the drive system so that the drive system rotates the frame relative to the exit guide about the rotational center, wherein rotation of the frame relative to the exit guide results in translation of the robotic scope out of the exit guide so that the robotic scope moves linearly away from the exit guide.

Any appropriate drive system may be used. For example, the drive system may include a robotic drive system such as one or more robotic arm. The robotic drive system may include a multi-degree of freedom robotic arm or more than one multi-degree of freedom robotic arm. The robot arm(s) may have any appropriate number of degrees of freedom (DOF), e.g., four DOF, five DOF, six DOF, seven DOF, etc. The robot arm joints may be rotary or pivoting, or they may be rectilinear. The drive system may be non-robotic, and may include, e.g., one or more motors and a controller. The drive system may move the frame in rotation (e.g., clockwise, counterclockwise, etc.) and/or may translate the frame and/or exit guide in space (e.g., in x, y, z, and any combination of angulations). The apparatuses described herein may simply be configured for use with the drive system or may include the drive system as part of the apparatus. In some examples the drive system may include a rotational drive that is controllable to drive the frame in rotation (e.g., clockwise, counterclockwise).

Similarly, any of the apparatuses described herein may be configured to work with a variety of elongate medical instruments (robotic scopes). However, in any of these apparatuses, the elongate medical instruments (e.g., robotic scope) may be included as part of the system.

Any of the apparatuses for storing and dispensing robotic scopes described herein may include a robotic scope mount configured to secure a proximal end of the robotic scope to the frame. For example, the robotic scope mount may comprise a clamp, clasps, etc. The robotic scope mount may include connections (electrical, pneumatic, water, motion, optical, etc.) for coupling to and/or controlling components of the robotic scope. For example, the robotic scope mount may be configured to couple the robotic scope to a pressure source.

In any of the methods and apparatuses described herein the securement is configured to hold (secure) the elongate medical instrument (e.g., scope, endoscope, etc.) either directly or indirectly to the frame so that it may rotate. The securement may be a channel, a magnetic attachment, a loop-and-hook (e.g., VELCRO) material, a plurality of tabs, snaps, undercuts, shear features, clasps, mechanisms, or an adhesive. The securement may be configured to hold the elongate medical instrument to the frame so that the elongate medical instrument may be held securely to the frame and controllably removed (detached) from the frame out of the exit guide when rotated in a first direction and re-attached to the frame and held securely when the frame is rotated in the opposite direction.

As mentioned, any of these apparatuses may include a removable tray configured to removably mate with the securement, wherein the removable tray is configured to hold the robotic scope.

The frame may have any appropriate shape, such as, e.g., a disk shape, a polyhedral shape (E.g., octagonal, etc.). In some examples, the frame is a wheel. The frame may be formed of a polymeric material (plastic), metallic material, or the like. In general, the frame may include a securement for holding the elongate medical instrument either directly or indirectly, such as for holding a tray that itself holds the elongate medical instrument. The frame may include one or more attachments for securing the tray and/or the elongate medical instrument to the frame. The frame may be relatively light weight and easy to clean. The frame may be single use disposable, or it may be multi-use.

Any of these apparatuses may include a support arm coupled to the exit guide and configured to secure the exit guide to the drive system. In general, the exit guide may be configured to engage with the elongate medical instrument as it is rotated out of (or into) the frame. Thus, the exit guide may be mounted adjacent to the frame and may slidably or movably engage or in close proximity to or with the frame, but generally does not move as the frame is rotated. In some examples the support arm holding the exit guide may be mounted to the drive system (e.g., a robotic arm) including to the same portion of the drives system that engages with the frame, so that they may be translated in space together, e.g., for positioning at or near the patient. In some examples the support arm may be moved or positioned by the drive system and/or manually.

The securement in the frame may extend partially or completely around the frame, including (but not limited to) around a peripheral region of the frame. In general, the securement may extend in an arc around the frame. The arc may have a constant radius or a changing radius (e.g., an increasing radius, etc.). The midpoint of the arc radius (the center point region of the arc) may be concurrent with the rotational center of the frame. In some examples the arc of the securement does not have a single center point, but may fall within a center point region; in some examples the arc of the securement does have a single center point. The securement may be any appropriate length so as to hold the elongate medical instrument. In some examples the securement extends at between 90 and 360 degrees, 540 degrees (or more) around the frame. The securement may include more than one complete wrap of the device. As this is accomplished, the additional length may be accomplished by a vertical stacking of the device as it passes itself for more than a 360-degree initial wrap, or by a horizontal stacking (radial inset or outlying). For example, the securement may extend more than 110 degrees, more than 140 degrees, more than 180 degrees, etc. around the frame.

In general, the rotation mount may be configured to couple the drive system to a region of the frame at a center point region of the arc formed by the securement.

As mentioned, any of these apparatuses may include the elongate medical instrument (e.g., the robotic scope). For example, the system may include the robotic scope, which may be a colonoscope. In some examples the robotic scope included with the apparatus is a rigidizable endoscope comprising a rigidizable inner member concentrically positioned within a rigidizable outer member. In general, any of these apparatuses may include a pressure input configured to couple the robotic scope to a pressure source to control rigidity of the robotic scope, including either or both an inner member and outer member in variations including inner and outer members.

In examples including an inner and an outer scope member, the outer scope member may be coupled to the frame (e.g., within the securement or a staring region of the securement) and the inner scope member may be coupled to an actuator for separately actuating the inner member of the robotic scope (e.g., inner robotic scope member). The inner member actuator may be part of the drive system and/or may be coupled with or mounted to the frame. In some examples the inner member actuator may be a driver mounted to the frame that moves (e.g., rotates through an arc) with or relative to the frame). In general, the inner member actuator may move with the frame, but may separately actuate movement of the inner member (e.g., in/out of the outer member). In general, the inner member actuator may include an inner scope mount to which an end region of the inner scope (e.g., the proximal region) may be coupled. The inner scope mount may comprise a clamp, clasps, etc. The inner scope mount may include connections (electrical, pneumatic, water, optical, etc.) for coupling to and/or controlling components of the inner member of the robotic scope. In some cases, the inner member of the robotic scope may be configured as an endoscope including imaging (e.g., light/fiber optics, imaging, working channels, suction channel(s), etc.). The inner scope mount may be configured to couple the robotic scope to a pressure source, e.g., for controllably rigidizing the inner member. For example, the inner scope mount may include a plurality of steering actuators configured to couple to a plurality of steering cables in the robotic scope, to drive bending (steering) of the inner member.

In some examples the inner member actuator is configured as a pivot arm that may include the inner scope mount, wherein the inner scope mount is configured to mount to a proximal end of an inner member of the robotic scope. The pivot arm may be configured to rotate the inner scope mount about the rotational center to move the inner member into or out of a distal end of an outer member of the robotic scope. In any of these examples, the pivot arm may be configured to rotate the inner scope mount relative to the frame over an arc (e.g., an arc that is 90 degrees or less, e.g., 80 degrees or less, 70 degrees or less, 60 degrees or less, 50 degrees or less, less, 40 degrees or less, 30 degrees or less, etc.). The angle of movement of the pivot arm as an input may result in the translation in linear movement of the inner member relative to the outer member at its output at the exit guide. In some examples the pivot arm is configured to couple to the drive system so that the drive system drives rotation of the pivot arm about the rotational center.

For example, described herein are systems for storing and dispensing a robotic scope, the system comprising: a frame; a rotation mount at a rotational center of the frame, wherein the rotation mount is configured to couple to a robotic arm for rotation of the frame about a rotational center; a securement extending radially around the frame in an arc, wherein the securement is configured to hold the robotic scope; an exit guide; and a support arm coupled to the exit guide and configured to secure the exit guide to the robotic arm so that the robotic arm rotates the frame about the rotational center relative to the exit guide, wherein rotation of the frame relative to the exit guide results in translation of the robotic scope out of the exit guide so that the robotic scope moves linearly away from the exit guide.

For example, a system for storing and dispensing a robotic scope may include: a frame; a mount at a rotational center of the frame, wherein the mount is configured to couple to a drive system so that the drive system rotates the frame about the rotational center; a securement extending radially around the frame in an arc, wherein the securement is configured to hold the robotic scope; an outer robotic scope mount configured to secure a first end of an outer member of the robotic scope to the frame; a pivot arm comprising an inner scope mount, wherein the inner scope mount is configured to mount to a first end of an inner member of the robotic scope, wherein the pivot arm is configured to rotate the inner scope mount about the rotational center to move the inner member into or out of a second end of the outer member of the robotic scope; an exit guide configured to mount to the drive system so that the drive system rotates the frame relative to the exit guide, wherein rotation of the frame relative to the exit guide linearly translates the robotic scope out of the exit guide so that the robotic scope moves linearly away from the exit guide.

For example, a system for storing and dispensing a robotic scope may include: a frame; a mount at a rotational center of the frame, wherein the mount is configured to couple to a robotic arm so that the robotic arm rotates the frame about the rotational center; a securement extending radially around the frame in an arc, wherein the securement is configured to hold the robotic scope; an outer robotic scope mount configured to secure a first end of an outer member of the robotic scope to the frame; a pivot arm comprising an inner scope mount, wherein the inner scope mount is configured to mount to a first end of an inner member of the robotic scope, wherein the pivot arm is configured to rotate the inner scope mount about the rotational center to move the inner member into or out of a second end of the outer member of the robotic scope; an exit guide configured to mount to the robotic arm so that the robotic arm rotates the frame relative to the exit guide, wherein rotation of the frame relative to the exit guide linearly translates the robotic scope out of the exit guide so that the robotic scope moves linearly away from the exit guide.

A system for storing and dispensing a robotic scope may include: a drive system; a frame mounted to the drive system at a rotational center of the frame so that the drive system rotates the frame about the rotational center; a securement extending radially around the frame in an arc, wherein the securement is configured to hold the robotic scope; an outer robotic scope mount configured to secure a first end of an outer member of the robotic scope to the frame; a pivot arm comprising an inner scope mount, wherein the inner scope mount is configured to mount to a first end of an inner member of the robotic scope, wherein the pivot arm is configured to rotate the inner scope mount about the rotational center to move the inner member into or out of a second end of the outer member of the robotic scope; an exit guide mounted to the drive system so that the drive system rotates the frame relative to the exit guide, wherein rotation of the frame relative to the exit guide linearly translates the robotic scope out of the exit guide so that the robotic scope moves linearly away from the exit guide.

Also described herein are cartridges configured to secure a robotic scope to a frame of any of the systems described herein. The tray may be pre-loaded with the robotic scope and may include a tray securement (e.g., tray channel or other securement) for holding the robotic scope. The tray may be configured to mate with the frame and may therefore include a protrusion on the back of the tray (the side not including the tray securement holding the robotic scope). The tray may include a protective cover covering the tray securement and/or the robotic scope stored therein. The tray may be lightweight; for example, the tray may be formed of a polymeric material. The tray may generally have a back side that is complementary to a side of the frame into which the tray is to be inserted (and secured). The frame may include one or more attachments (e.g., securements, etc.) to hold the tray in position.

Also described herein are methods of using any of these apparatuses. For example, described herein are methods of dispensing a robotic scope, the method comprising: rotating a frame about a rotational center of the frame relative to an exit guide, so that the robotic scope held within a securement that extends radially around the frame is directed by the exit guide to extend linearly from the exit guide, wherein rotation of the frame relative to the exit guide translates rotational movement of the robotic scope into linear movement of the robotic scope. Any of these methods may optionally include securing a tray holding the robotic scope into the securement. Any of these methods may include coupling a first end of the robotic scope to a robotic scope mount so that the robotic scope is secured to the frame.

In general, these methods may include comprising coupling an outer rigidizing member of the robotic scope to an outer robotic scope mount on the frame.

Any of these methods may include actuating an inner scope actuator (e.g., a pivot arm) such as pivoting the pivot arm about the rotational center to move an inner member of the robotic scope into or out of an end of an outer member of the robotic scope.

Any of these methods may also include coupling an inner rigidizing member of the robotic scope to an inner scope mount.

In some examples the method may include steering bending of a distal end region of the robotic scope. Rotating the frame may comprise driving a robotic arm to rotate the frame relative to the exit guide.

For example, a method of dispensing a robotic scope may include: securing a tray holding the robotic scope into a securement extending radially around a frame coupled to a robotic arm; and driving the robotic arm to rotate the frame about a rotational center of the frame relative to an exit guide, so that the robotic scope extends linearly from the exit guide.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 5C shows an enlarged view of a portion of the system for storing and dispensing a robotic scope shown in FIG. 5A, showing the exit guide.

FIGS. 5D and 5E illustrate enlarged views of the exit guide engaging with retainer(s) on the frame.

FIGS. 14A-14D schematically illustrate an example of a linear system for dispensing a robotic scope having a robot arm with some pivoting or rotary joints and some rectilinear joints.

FIGS. 17A-17E schematically illustrate an example of a linear system for dispensing a robotic scope having a turn towards a vertical orientation (e.g., up to a 90 degree or more turn), and a bed-mounted robot arm.

DETAILED DESCRIPTION

Figure 1A:
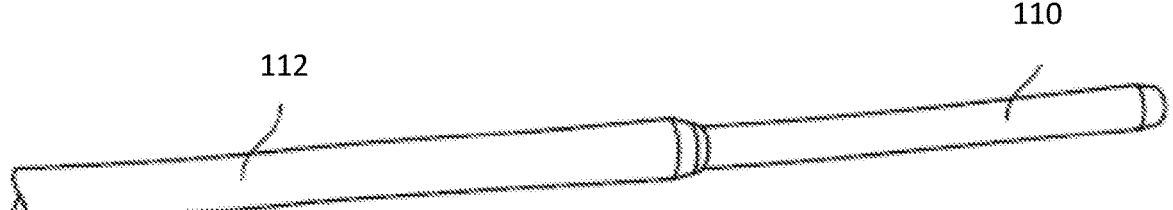
FIGS. 1A-1D illustrate one example of an elongate medical instrument, such as a robotic scope, that may be used with the methods and apparatuses described herein. The elongate medical instrument in this example is an endoscope having an inner member and an outer member that are both selectively rigidizing.

Aspects of the present disclosure may be integrated into a robotically-enabled medical system capable of performing a variety of medical procedures, including both minimally invasive procedures-such as laparoscopy- and non-invasive procedures-such as endoscopy. Among endoscopy procedures, the system may be capable of performing colonoscopy, enteroscopy, bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user. An apparatus (e.g., a system, devices, etc.) for storing and/or dispensing a robotic scope may be configured to hold the robotic scope in a compact or coiled (or partially coiled configuration) and may robotically dispense and control the operation of the robotic scope.

In particular, described herein are rotational systems for dispensing and/or storing robotic scopes. These systems may include a frame that may include a securement; the securement may extend in an arc around the frame. In some examples the frame may be configured to hold the robotic scope so that rotation of the frame by a drive system (or drive sub-system) may extend or retract the scope so that it may be directed into (or out of) a body. Thus, these apparatuses may be configured to convert rotational motion into a linear motion. The apparatus may also control operations of the robotic scope, including steering of the scope or a portion of the scope. The apparatus may also control operations of the robotic scope and an overtube, including rolling either or both about their cylindrical central axis. In some examples, the apparatus may include selectively rigidizing the scope or portions of the scope.

For example, a rotational system may include a frame that may be mounted at a rotational center of the frame to a drive system (or in any of these examples, drive sub-system). The frame may be rotated about a rotational center of the frame. The frame may also include a securement extending radially around the frame in an arc. This securement may be configured to hold the robotic scope, which may couple to the frame. The apparatus may also include an exit guide that is also mounted or configured to mount to the drive system. The drive system may be operated to rotate the frame relative to the exit guide so that the robotic scope extends linearly out of the exit guide.

The methods and apparatuses described herein may include a securement that is configured to hold (secure) the elongate medical instrument, e.g., scope, endoscope, etc., either directly or indirectly to the frame so that the elongate medical instrument rotates with the frame. The securement may be a mechanical securement, e.g., including one or more contacts for holding the elongate medical instrument to the frame. These contacts may be projections from the frame or recessed into the frame. For example, the securement may be a channel such as a an open (or U-shaped) channel, a plurality of clips, tabs or projections arranged to hold the elongate medical instrument to the frame, etc. In some examples the securement may engage or mate with a complimentary region on the elongate medical instrument to the frame, for example, the securement may include a loop-and-hook (e.g., VELCRO) material. In some examples the securement is an adhesive securement that releasably secures the elongate medical instrument to the frame via an adhesive (including low-tack adhesives materials that may release and re-engage the elongate medical instrument to the frame multiple times). In some examples the securement is a magnetic attachment that magnetically couples the elongate medical instrument to the frame. For example, a magnetic securement may include magnets that releasably hold the elongate medical instrument; the elongate medical instrument may include magnets or materials that will be attracted to magnets (e.g., ferromagnetic materials). In general, the securement may hold the elongate medical instrument to the frame so that the elongate medical instrument may be controllably detached from the frame out of the exit guide when rotated in a first direction and may be controllably re-attached to the frame and held securely when the frame is rotated in the opposite direction.

In some examples these apparatuses may be referred to as rotary storage and dispensing system ("RSDS") and may be used to store and dispense the robotic scope. These methods and apparatuses described herein may be used with any elongate medical instrument, including robotic scopes, and in particular, endoscopes. Many of the examples of robotic scopes described herein are shown as robotic endoscopes include nested, telescoping components, so that each robotic scope includes a "mother" (e.g., an outer member) and a child (e.g., an inner member). In some examples these robotic endoscopes are dual rigidizing endoscopes in which the inner member (child) nests inside the outer member (mother), and allows for steerable and stable advancement using an inch-worming technique that may take advantage of the ability to controllably rigidize either or both the outer member and the inner member.

Figure 1B:
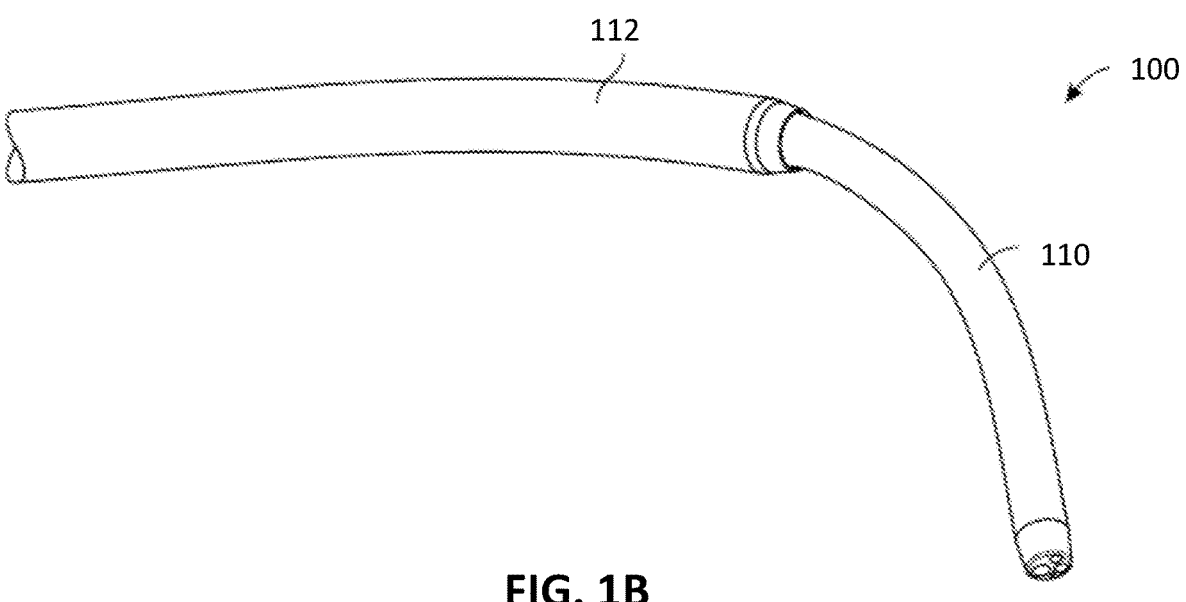
Figure 1C:
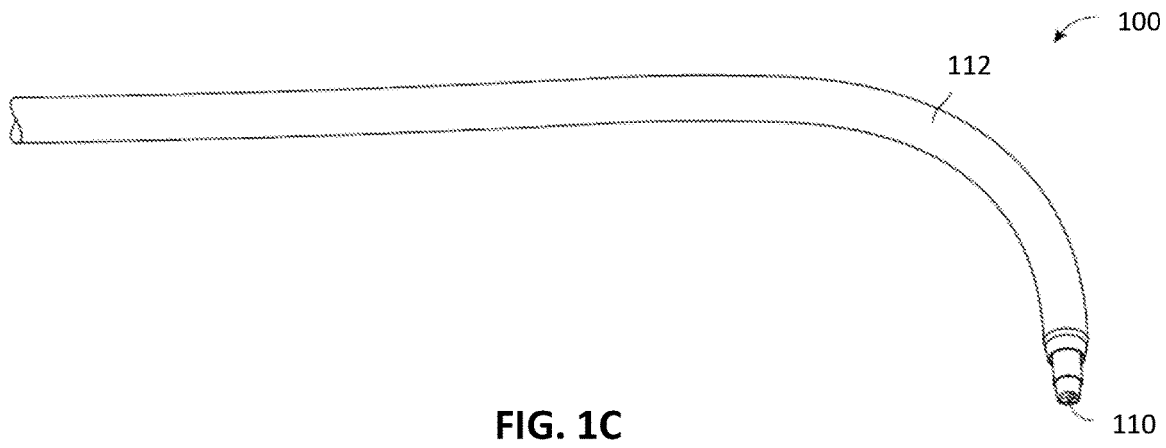
Figure 1D:
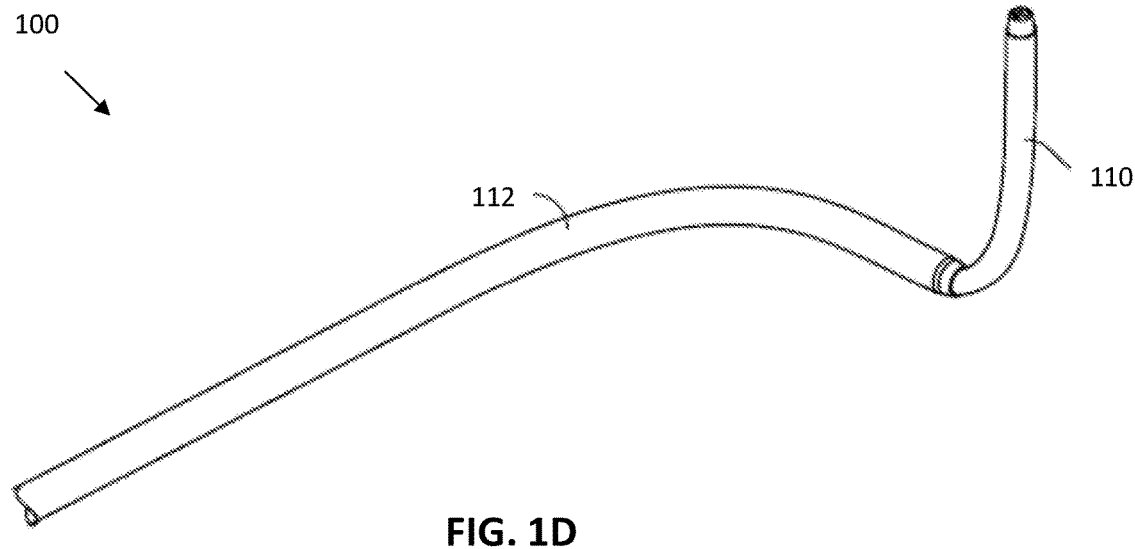

For example, FIGS. 1A-1D illustrate one example of a robotic scope configured as a dual rigidizing endoscope. In FIGS. 1A-1D, the dual rigidizing endoscope 100 is config-ured as a nested system including a rigidizable (e.g., rigidiz-ing) outer member 112 and a rigidizable inner member 110. In FIG. 1A, the steerable inner rigidizing member 110 is positioned within the outer rigidizing member 112 such that the distal end of the inner rigidizing member 110 extends outside of the outer rigidizing member. In some cases the inner rigidizing member 110 may be fully retracted into the outer rigidizing member 112. FIG. 1B shows the distal end of the inner rigidizing member 112 is bent slightly in a desired direction/orientation (e.g., via steering cables or other steering mechanism) and then rigidized (e.g., using positive or negative pressure). 112 may also be bent because it was in the flexible state as it followed the curvature of 110, and then was subsequently rigidized. In FIG. 1C, the outer rigidizing member 112 (in the flexible configuration) is advanced over the rigidized inner rigidizing member 110 (including over the bending distal section). Once the distal end of the outer rigidizing member 100 is sufficiently advanced over the distal end of the inner rigidizing member 110, then the outer rigidizing member 112 can be rigidized (e.g., using positive or negative pressure as described herein). In FIG. 1D, the inner rigidizing member 110 can then be transitioned to the flexible state (e.g., by removing the positive or negative pressure in some examples, and by allowing the steering cables to go slack such that tip can move easily) and can be advanced and directed/oriented/ steered as desired. Alternately, in FIG. 1D, the inner rigidiz-ing member 110 can be actively steered (either manually or via computational control) as it emerges such that is mini-mizes the load on the rigidized outer tube. Minimizing the load on the outer rigidizing member may make it easier for this tube to hold the rigidized shape. Once the inner rigidiz-ing member 110 is rigidized, the outer rigidizing member 112 can be transitioned to the flexible state and advanced thereover. The process can then be repeated to navigate through even more tortious anatomies. However, it may be particularly difficult to coordinate the movement of the inner and outer members, including advancing/retracting and selectively rigidizing either the inner or outer or both, making a robotically controlled system particularly advan-tageous. The repeated process can result in "shape copying," whereby the inner and outer rigidizing members, while in a flexible configuration, may continuously conform to (or copy) the shape of whichever member is in the rigid con-figuration.

The example of a robotic scope shown in FIGS. 1A-1D illustrate the operation of just one type of medical instru-ment that may be used with the methods and apparatuses described herein. Furthermore, these apparatuses may be configured so as to function as endoscopes, including one or more of imaging, irrigation, lighting, steering channels for removing or applying materials, etc. For example, the robotic scope 100 may be a "navigation" device comprising a camera, lighting and a distal steering section. The navi-gation device (scope or portion of a scope) may be well sealed such that it is easy to clean between procedures. In some examples it does not need to be cleaned because it is fully sheathed, including both on the outside and through the working channels. In some examples a second inner device may then be placed inside the rigidized outer member and advanced past the distal end of the outer member. The second inner member may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract.

In some examples, the rigidizing members described herein can transition from a flexible configuration to a rigid configuration and the stiffness may be considered "variable stiffness" as it may be selected by the user or system. For example, each rigidizing member may be rigidized by applying a positive or negative pressure to the wall of the rigidizing member or within the wall of the rigidizing member. With the positive or negative pressure removed (or reversed), the layers can easily shear or move relative to each other; the release of the positive or negative pressure may allow the layers to transition to a condition in which they exhibit a substantially enhanced ability to resist shear, movement, bending, torque and buckling, thereby providing system rigidization. Although the examples shown above in the described apparatuses that rigidize by the application of pressure (e.g., positive or negative pressure), the methods and apparatuses described herein may be used with any appropriate rigidizable member(s), not limited to positive or negative pressure rigidizing apparatuses. For example, the rigidizable members described herein may refer to any appropriate rigidizing device, including members that may be rigidized by jamming particles, by phase change and/or shape memory alloys, by interlocking components (e.g., cables with discs or cones, etc.), EAP (electro-active poly-mers) or any other rigidizing mechanism.

Any of the rigidizable apparatuses described herein may include rigidizing layers or regions that engage with a compression layer (which may be or may include a bladder) that applies force to the rigidizing layer to rigidize the rigidizing layer or in some cases to de-rigidize (e.g., release from rigidization) the rigidizing layer. In some examples, these rigidizable apparatuses may include a rigidizing layer that could include a braid, knit, woven, chopped segments, randomly distributed or randomly oriented filaments or strands, engagers, links, scales, plates, segments, particles, granules, crossing filaments, or other materials forming the rigidizing layer. For example, the rigidizing layer may comprise multiple strand lengths or strand segments that cross over each other (e.g., as part of a braid, knit, woven, etc.); the compression layer may apply force to drive the crossing strand lengths or strand segments against each other. Although many of the examples shown herein are braids, any of these apparatuses may instead or in addition include a general rigidizing layer comprising crossing strand lengths or strand segments. The examples of rigidizing apparatuses described herein may use pressure (positive pressure) and/or negative pressure to selectively and con-trollable rigidize. In some examples the method described herein may be used with any appropriate rigidizing appara-tus.

A sequence identical to or similar to that illustrated in FIGS. 1A-1D may be performed by the apparatuses described herein, including in particular, the rotational sys-tems described herein.

In general, the robotic scopes may be actively steered automatically or manually, including by a user operating the apparatus, so that the robotic scope is steered into known, assumed, or measured shapes, when advanced into the anatomy. This may be particularly useful and important when navigating a dual rigidizing endoscope such as (but not limited to) that shown in FIGS. 1A-1D. For example, a distal tip of the inner rigidizing member can be steered (including steering to set or match a shape of the section of the outer rigidizing member). Typically, a region of the inner and/or outer members of the scope may be steered at a region immediately proximal to the distal tip.

Thus, generally, the apparatuses described herein may include effectors for controlling operation of the scope operated by the device, including for steering, rigidizing, navigation, imaging, lighting, etc. For example, the effectors (e.g., end effectors) of some variations of the system's robotic arms may include an instrument driver that may incorporate electro-mechanical means for actuating (e.g., steering) the medical instrument and may include a mount for detachably coupling to the scope or portion of the scope (e.g., inner member, outer member, etc.). For example, PCT application PCT/US2023/064999, filed Mar. 27, 2023, and titled "METHODS AND APPARATUSES FOR NAVIGAT-ING USING A PAIR OF RIGIDIZING DEVICES," describes examples of apparatuses including nested apparatus that may be used with any of the methods and apparatuses described herein. Other examples of apparatuses that may be used with the methods and apparatuses described herein may include nested catheters such as those described, for example, in U.S. patent application Ser. No. 17/902,770, tiled "NESTED RIGIDIZING DEVICES," filed on Sep. 8, 2022, U.S. patent application Ser. No. 18/000,062, titled "RIGIDIZING DEVICES," filed on May 26, 2021, patent application no. PCT/US2022/014497, titled, "DEVICES AND METHODS TO PREVENT INADVERTENT MOTION OF DYNAMICALLY RIGIDIZING DEVICES," filed on Jan. 31, 2022, patent application no. PCT/US2022/082300, titled "METHODS AND APPARATUSES FOR REDUCING CURVATURE OF A COLON," filed on Dec. 22, 2022, patent application no. PCT/US2023/062206, titled "DYNAMICALLY RIGIDIZING COMPOSITE MEDI-CAL STRUCTURES," filed on Feb. 8, 2023. Each of these applications are herein incorporated by reference in their entirety.

Figure 2:
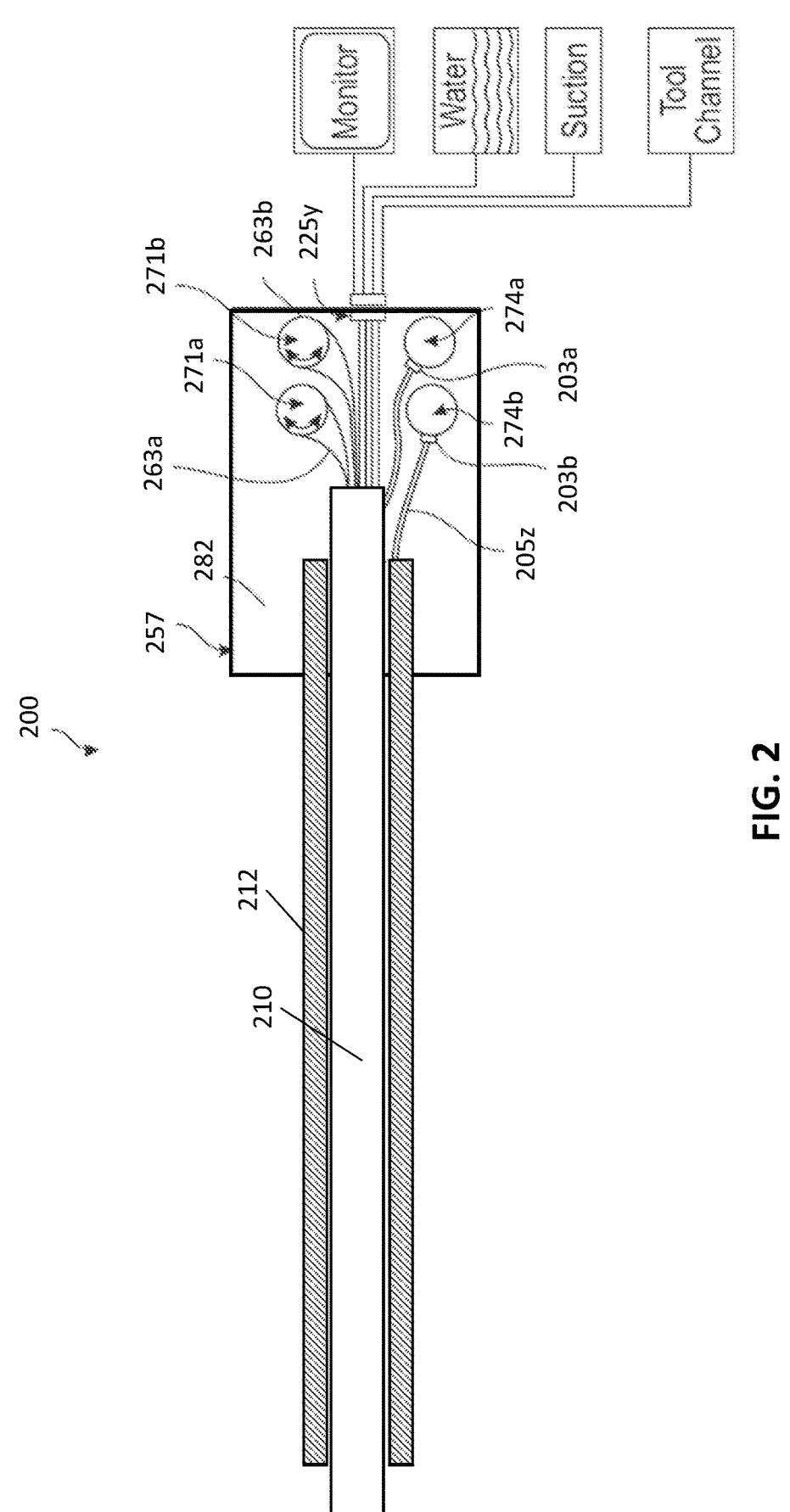
FIG. 2 shows an example of a mechanism for actuating an elongate medical instrument similar to that shown in FIGS. 1A-1D.

In some examples, the robotic scope, such as a dual rigidizing apparatus shown in FIGS. 1A-1D may be roboti-cally controlled. For example, the proximate end(s) of the robotic scope may include connection for connecting the robotic scope to a frame. In the example shown in FIGS. 1A-1D, the outer rigidizing member 112 and the inner rigidizing member 110 may each include controls and/or connections for coupling to steering inputs, air lines (e.g., suction), water lines, video lines (e.g., monitors, et.), and/or one or more tool channels. In some examples the robotic scope proximal end (or in the case of a dual rigidizing scope, each of the inner and outer members) may include a con-nector region, such as a cassette 257, shown schematically in FIG. 2. Each of the inner and outer members may include a separate cassette.

For example, the cassette may include connections for controlling steering, e.g., by one or more steering tendons, within the inner and/or outer members. For example, the cassette 257 can include disks 271a, 271b that may connect to cables 263a,b respectively, to steer (e.g., bend or deflect) the tip of the inner rigidizing member 210. Other steering mechanisms (e.g., pneumatics, hydraulics, shape memory alloys, EAP (electro-active polymers), or motors) are also possible. Again, in examples with different steering mecha-nisms, one or more disks in the cassette 257 (e.g., disks 271a, 271b) may be used to actuate the steering.

The cassette 257 can further include pressurization con-nections 203a, 203b that may connect to a pressure source for rigidizing the inner and/or outer members, respectively. Pressure (positive or negative, depending on the robotic scope, may pass through pressure lines 205z, causing the pressure in a pressure gap of the inner rigidizing member 210 to change (e.g., increase under positive pressure or decrease under negative pressure, i.e. vacuum), causing the rigidizing devices 210, 212 to become rigid. Activation of the pressure (positive or negative) may be applied sequen-tially and/or simultaneously, as illustrated in FIGS. 1A-1D. In some examples the cassette 257 can include pressure connectors 274a,b to sealingly couple to the one or more pressure sources. Other mechanisms causing rigidization of the robotic scope (e.g., inner and outer rigidizing members) are also possible.

The cassette 257 can include a connector for connecting to additional lumens and/or wiring in the outer or inner rigidizing device(s). For example, in FIG. 2 the cartridge 257 is coupled to the inner rigidizing member 110 and the connector 225y may include a connection for the delivery of both suction and water to the tip of the inner rigidizing device. The connector 225y may include an electrical con-nector to connect to a camera mounted to the tip of inner rigidizing device 110 to an external monitor and/or video processing unit. The connector 225y may include a mechani-cal connector that connects to a hollow tube (e.g., working channel) leading all the way to the tip of the inner rigidizing device 210. By including the connector 225y, the control of all components of the system 200 can be performed through the cassette 257 and may be manually or automatically controlled by the apparatuses described herein.

In some examples the control connections (e.g., disks 289, 271a, 271b, etc.) may be accessible from a bottom of the cassette 257. The control connectors may have features, such as splines, pins or teeth, to transmit torque. These features can allow them to be manipulated (e.g., by a drive system).

Figure 3:
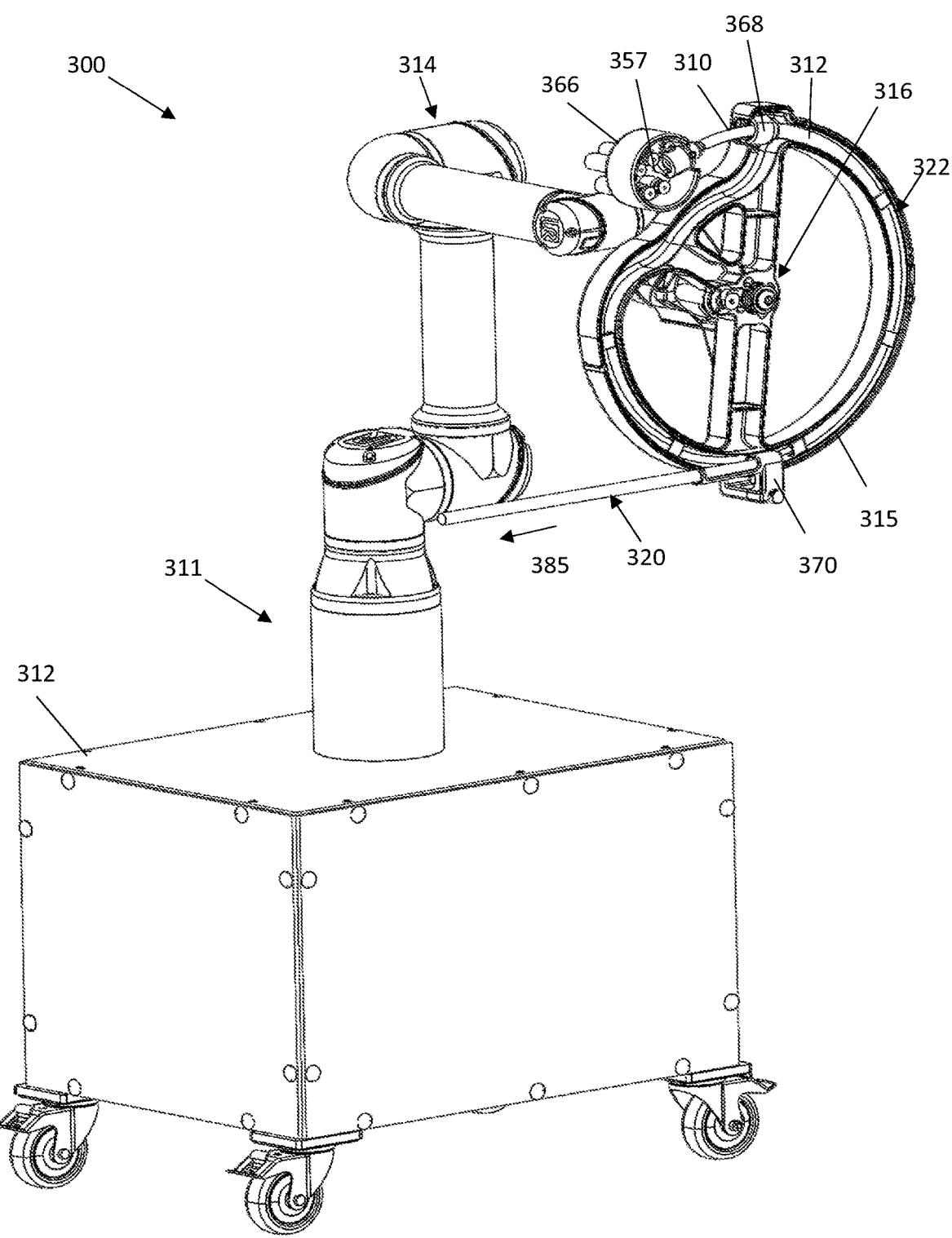
FIG. 3 schematically illustrates one example of a system for storing and dispensing a robotic scope as described herein, utilizing a robotic arm with rotary joints.

FIG. 3 illustrates a first example of an apparatus (e.g., a system) for storing and dispensing a robotic scope 300. In this example, the system 300 includes a drive system 311. The drive system in this example includes a robotic arm 314 that is configured to operate as a multi-degree of freedom (DOF) apparatus. The arm may be moved in space (x, y, z, and angulations from axes) and may include one or more rotational drives (e.g., on the end of the robotic arm). The drive system in this example is shown mounted to a cart 312 having wheels allowing the cart to be positioned by rolling, e.g., near the bedside. In some examples the drive system may be a rotational drive system that does not necessarily include a robot arm.

The example apparatus shown in FIG. 3 also includes a frame 315 mounted to the drive system at a rotational center of the frame so that the drive system rotates the frame about the rotational center. For example, a mount 316 for coupling the frame to the drive system may be positioned at the rotational center. In FIG. 3 a robotic scope 320 is shown positioned within a securement 322 of the frame 315. The securement 322 in the frame 315 extends radially around the frame in an arc. In general, this securement 315 is configured to hold the robotic scope 320. In the example shown in FIG. 3 the securement is a channel, and specifically a U-shaped open channel. The frame can be rotated by the activation of a motor, with multiple methods. One example is to insert a harmonic drive in the center of the mount, 316.

The securement can be created such that the device has less than 360 degrees of wrap. The securement can be created such that the device has more than 360 degrees of wrap. For example, as the device completes 360 degrees of wrap, it can be adjacently coiled radially inward or outward, thereby enabling a longer device in a smaller diameter (for example, 450, 540, 630 or 720 degrees of wrap, or more, including any degree between). Similarly, the device can complete 360 degrees of wrap and then can be adjacently coiled with the same radial wrap, but in a different plane, for example, against the backplane surface of 322. This thereby enables a longer device in a smaller diameter (for example, 450, 540, 630 or 720 degrees of wrap, etc.).

The example of the robotic scope shown in FIG. 3 includes an inner rigidizing member 310 and an outer rigidizing member 312. The outer rigidizing member is coupled to the frame by an outer robotic scope mount 368 that is configured to secure a first (e.g., proximal) end of the outer member 312 of the robotic scope 320 to the frame 315. In this example the outer robotic scope mount 368 is a clamp. The outer robotic scope mount may also include a connection or coupling to interface one or more elements of the outer rigidizing member. For example, the outer rigidizing member may also be coupled to a source of pressure (e.g., positive or negative pressure) for rigidizing.

Any of these apparatuses may be configured to provide rotation of the inner rigidizing member 310 and/or the outer rigidizing member 312 in roll, e.g., about the long axis of the elongate tubular body of the inner rigidizing member 310 and/or an outer rigidizing member 312. In some examples either the inner rigidizing member 310 and/or an outer rigidizing member 312 may be configured to be sufficiently torsionally stiff so that applying roll at the back (proximal) end may result in roll at the distal end region. For example, in FIG. 3, the apparatus may be configured to move the inner scope mount 366 in roll to roll the inner rigidizing member 310 from the proximal end relative to the outer rigidizing member. In some examples both the inner and outer rigidizing members may be rolled by moving the robotic arm 314 so that the frame 315 holding the outer and inner rigidizing member is rotated about linear exit region (e.g., exit guide 370). The inner rigidizing member in this example includes a cassette 357 to connect the inner rigidizing member at its proximal end to the drive system, so that the drive can be applied to actuate (e.g., steer) the distal end of the inner rigidizing member (see, also FIG. 7 for additional detail). Thus, the cassette may be configured to make connections to effectors in the drive system. In this example, the connections are made through an inner scope mount 366 that is part of a pivot arm that extends from drive system and is configured to rotate the inner scope mount about the rotational center to move the inner member into or out of a second end of the outer member of the robotic scope.

The system 300 shown in FIG. 3 also includes an exit guide 370 mounted to the drive system 311 (e.g., via a support arm 571 extending from the drive system as shown in FIG. 5C, below) so that the drive system rotates the frame 315 relative to the exit guide 370. This rotation of the frame 315 relative to the exit guide 370 result in the linear translation of the robotic scope 320 out of the exit guide so that the robotic scope moves linearly 385 away from the exit guide. The exit guide is shown as being nearly tangential to the bottom of the wheel's arc. However, the exit guide can also be positioned such that it is further along the arc of the wheel, e.g., up from the bottom. For example, it could be at a location 30 or 45 degrees further along the wheel's arc, such that the device's exit from the exit guide has a smaller axial offset from the entry point into the patient's anus. In this example, the drive system (e.g., robot arm) has a rotary motion output that controls the rotation of the frame, which is shown configured as a wheel structure. The drive system therefore dispensing the robotic scope (e.g., the outer or mother member and the inner or child member) from a coiled or circular stored configuration to the "in use" linear profile. The non-rotating exit guide (or guide tube) positioned at the bottom of the frame is attached to a support arm (e.g., guide tube support arm). This support arm may thus be used to direct the motion of the robotic scope as it leaves the frame.

Figure 4A:
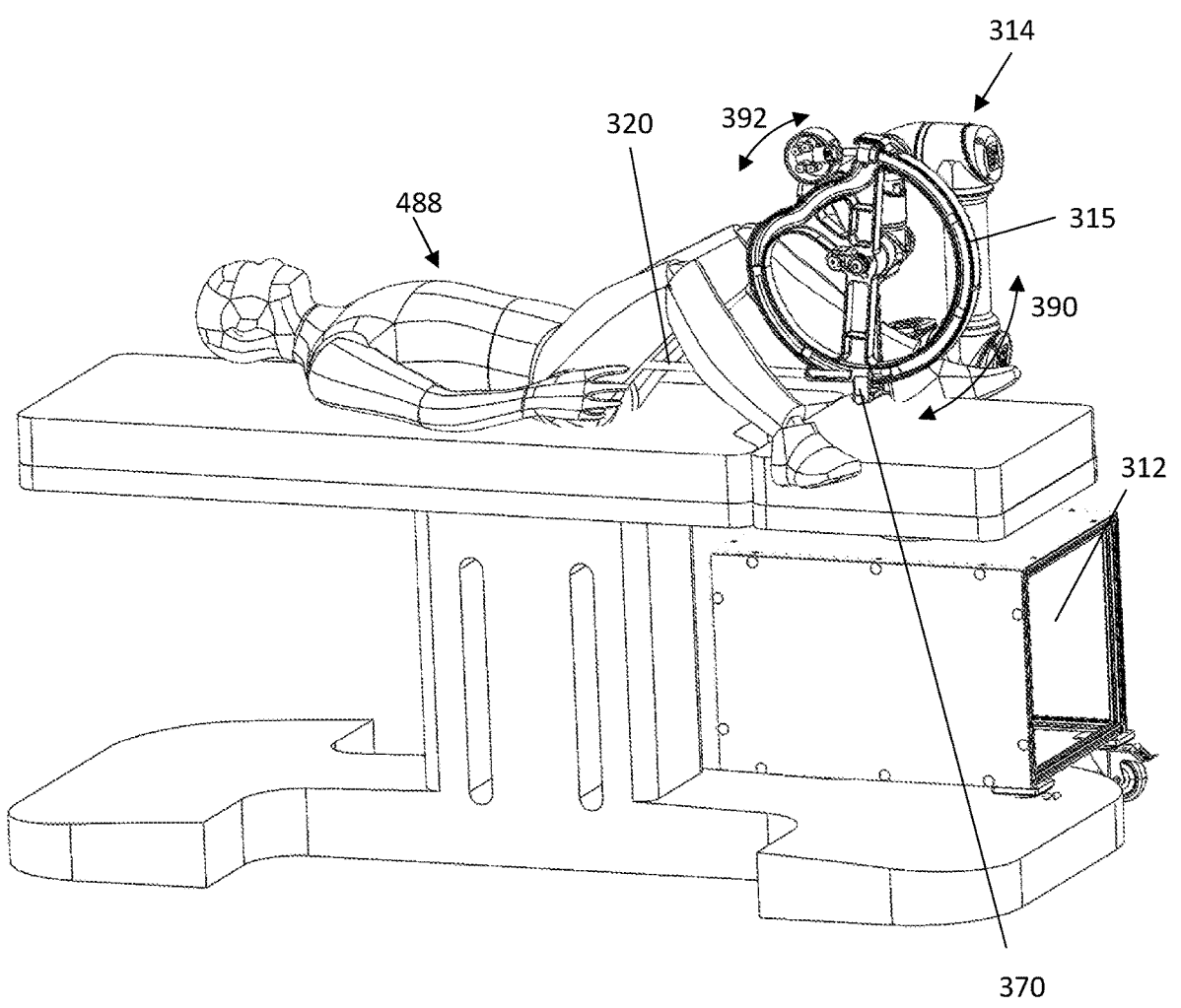
FIGS. 4A-4D illustrates examples of a system for storing and dispensing a robotic scope similar to that shown in FIG. 3 positioned to treat a patient, showing the patient being treated in different positions.

This is illustrated in FIG. 4A. In FIG. 4A a patient 488 is shown lying on their back on a table. An apparatus similar to the one shown in FIG. 3 is shown adjacent to the table so that the cart 312 to which the drive system (drive subsystem) 311 is mounted. The drive system in this example includes a robotic arm to which the frame 315 has been mounted at a center of rotation of the frame. The robotic arm 314 may therefore rotate 390 the frame 315 while holding the position of the exit guide 370 relatively fixed, causing the robotic scope 320 to extend linearly from the frame 315 so that it may be directed into the patient's body. As mentioned above, the drive system (robotic arm) may also separately drive the inner member of the robotic scope by mounting the proximal end of the inner member to an inner scope mount that is coupled to a drive (e.g., pivot arm). As the pivot arm pivots, it moves the inner scope mount 392 (and thus the end of the inner member) relative to the outer member, allowing the inner member to move in or out relative to the outer member. The inner member may therefore move independently of the outer member by moving the pivot arm relative to the wheel. This actuated back-and-forth motion between the inner and outer members may be coordinated with the rigidization of these members and may allow for the inchworm drive of the dual rigidization robotic scope. In the dual rigidization systems described herein, when the inner or outer members are made rigid, the system may hold their position relative to the patient constant. For example, when the inner member is rigid (e.g., by the application of positive or negative pressure) the pivot arm may be configured to remain in a fixed position relative to the patient, while allowing rotation of the frame and therefore advancing/retraction of the flexible (non-rigid) outer member. Similarly, if the outer member is rigid, the rotation of the frame relative to the patient (and the position of the exit guide relative to the patient) may be fixed while the pivot arm is allowed to move and thereby advance or retract the inner member. In any of the apparatuses described herein, when the robotic scope is a rigidizing (e.g., dual rigidizing) scope, the arcing securement through the frame may have a constant radius, and the center point of the arc may be the rotational center for the frame.

In any of these examples the table or bed may include a top mat that has a thickness to help raise the patient off of the table surface. This mat may have a thickness, e.g., about one, 2, 4, 8, 10, or 12 inches thick. The mat could have a region (e.g., notch or quadrant) of material removed so that the frame can advance into that space, such that it can effectively have a reduced net height relative to the top of the mat. This could be advantageous, as less vertical leg manipulation of the patient would be necessary as they change position. This could also be coupled to the exit guide being configured such that it exits from the top quadrant of the frame, rather than the bottom quadrant.

In the example shown in FIGS. 3 and 4A-4D, the pivot arm and the inner scope mount may include steering motors, controls for roll, robotic tools, and tool access ports.

In general, the frame may be configured as a wheel, and can be configured so that it can readily be removed from the drive system (e.g., robotic arm(s)), so that it could be readily cleaned, for example, in a standard hospital sanitizing washing machine. The frame may be configured so that it has minimal (or no) electronics or motors, for simplifying cleaning. In one example, the pivot arm has two parts (two arms): one that pivots, and one that co-joins to the frame (the 'co-joining pivot arm'). As the frame is attached, for example, it can have recessed features into which mating male features (for example, pins), insert. Therefore, the two elements (frame and co-joining pivot arm) can be co-joined so that as one of the pivot arm moves (for example, with a motor geared down to a lead screw that goes across the arc between both arms), it moves the other arm relative to the frame. The co-joining pivot arm can also have a motor so that it can provide 'roll' axis control of the outer tube. It can also have fittings to connect, so that the outer tube's rigidization can be controlled.

Figure 4B:
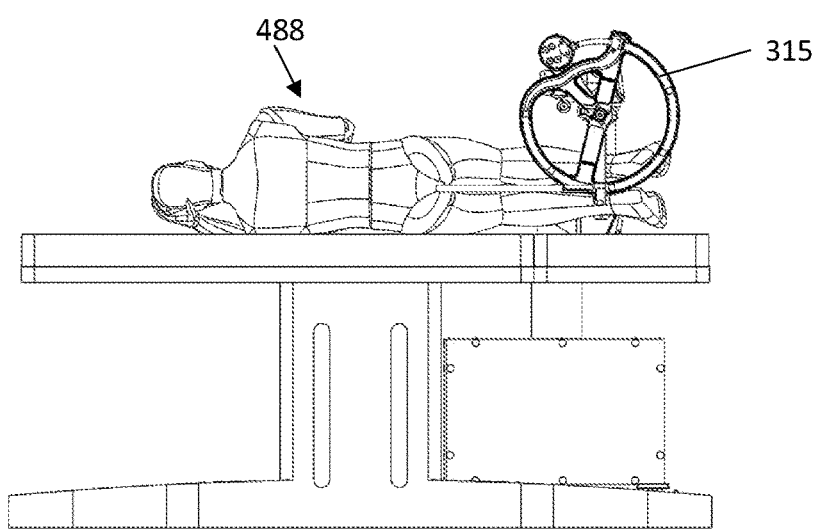
Figure 4C:
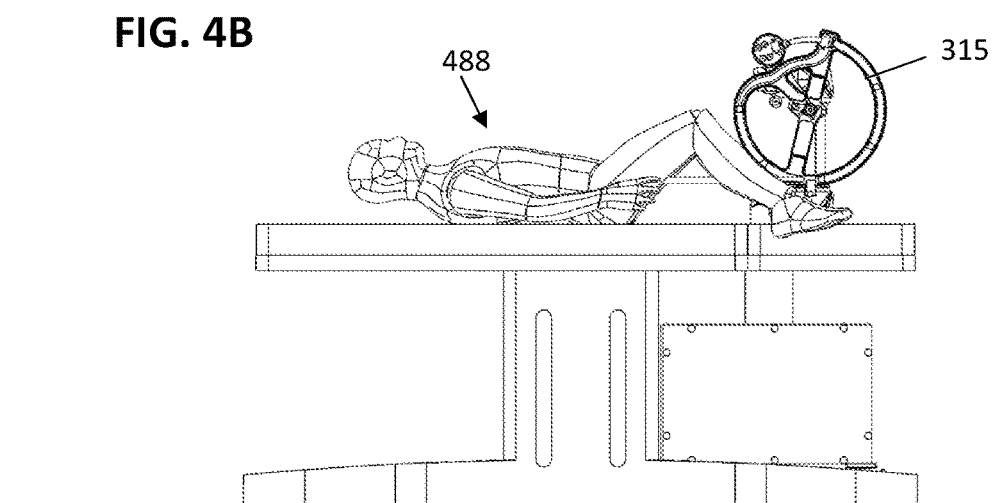
Figure 4D:
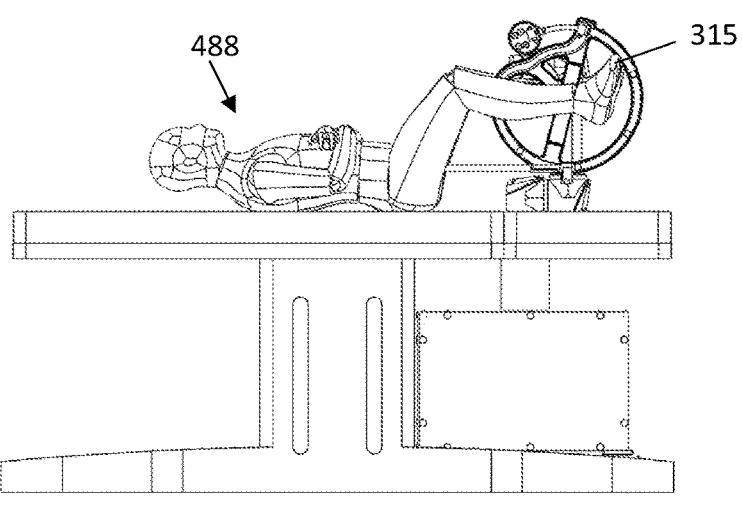

FIGS. 4B-4D illustrate other possible positions that the apparatus may be operated in. Because these devices may take so little space, they may be operated with the patient in virtually any position. For example, FIG. 4B shows the patient 488 on their side, in a left lateral position. FIG. 4C shows the patient 488 on their back, in a dorsal recumbent position. FIG. 4D shows the patient 488 in a lithotomy position, with legs up (e.g., in stirrups). Additionally, the frame can be rotated on the robotic arm so that the frame can be, for example, oriented parallel to the table. This could be an advantageous orientation relative to loading and unloading the system.

Figures 5A, 5B:
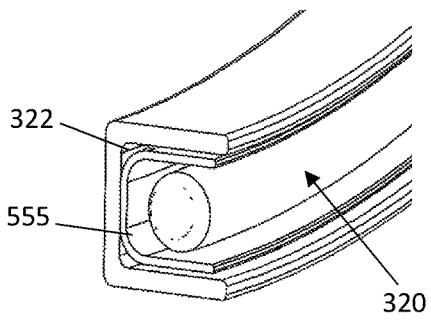
FIG. 5A shows an example of a system for storing and dispensing a robotic scope as described herein.
FIG. 5B is a view through a section of securement (shown in this example as an open or u-shaped channel) of the system for storing and dispensing a robotic scope shown in FIG. 5A.

FIGS. 5A-5C show additional detail for a system similar to that shown in FIG. 3. In FIG. 5A the system includes the frame 315 having a securement 322. The securement is configured to hold the robotic scope 320. In this example, the securement indirectly holds the robotic scope in the securement, as the robotic scope 320 is held in a tray 555 that is mated into the securement 322 of frame 315. This is shown in the partial sectional view of FIG. 5B. FIG. 5A also includes a pivot arm 565 to which an inner scope mount 366 is coupled and through which the inner member 310 of the scope 320 is coupled. The outer member 312 is coupled to the outer robotic scope mount 368.

The frame may include one or more retainers (e.g., retention tabs) to hold the scope in the securement (or to hold both the tray and the scope in the securement in some examples). The retainers may be part of the securement. For example, in FIG. 5A retention tabs 573 are utilized to hold the scope in the securement (channel 322) of the tray 555. In some examples a single (e.g., continuous) retainer may be used. In some examples a plurality of discrete retainers (e.g., retention tabs) can be used. The retainer(s) may be constructed so that they can be deflected out of the way by as the scope (e.g., outer member 312) enters and then exits the exit guide 370. For example, the retainer(s) may be formed of an elastomeric or a plastic material that can be deflected without yielding, e.g., by the ramp geometry of the exit guide. In some examples the retainer(s) can be cantilevered from one side, or they can extend from each side of the channel, e.g., meeting at or near the middle of the channel. In some examples the retainers (e.g., tabs) are used as the securement without the need for an additional channel.

For example, FIGS. 5D and 5E show two views of a portion of a frame 315 that includes retainers (e.g., retainer tabs 573) that extend partially from the radially inward side of the securement (e.g., channel) across towards the radial outward side of the securement to retain the scope 320 within the channel (or within the tray channel that is sitting in the channel). In this example, the tabs are configured to be deflected away from the channel by the exit guide 370 that includes a ramp 573 surface that deflects the tab, which may ride up and over the ramp at the end of the exit guide 370, so that the scope may be uncoupled from the securement of the frame and to exit out of the exit guide. In some examples there is a ramp on both the input and output sides of the exit guide 370 (e.g., both the distal-facing and proximal-facing sides), so that the retainers, e.g., retainer tabs, can be displaced over the exit guide as the frame is rotated both clockwise and counter-clockwise.

FIG. 5C illustrates an enlarged view of the exit guide 370 that is separately mounted to a support arm 571 so that it may remain stationary relative to the patient (or may move independently of) the rotation of the frame 315. As described above, this rotation relative to the exit guide 370 may result in converting the rotational movement of the frame into linear movement of the scope 320.

In some examples the frame (and scope) may be disposable. In other examples, portions of the frame may be reusable, particularly when a tray is used. In any of these examples the tray may incorporate one or more retainers (retention tables, flanges, etc.) or other attachment features. For example, the outer member (the mother member) may be included within a tray that can be house the outer member during sterilization and shipment. In general, the tray with the outer member and the wheel may have multiple potential configurations. In some examples the tray may be positioned within a sterilizable container (e.g., a Tyvek pouch) so that it may be sterilized and stored in a sterile container. As the container (e.g., pouch) is removed, the tray with its constituent elements can be loaded within the frame.

Figure 6A:
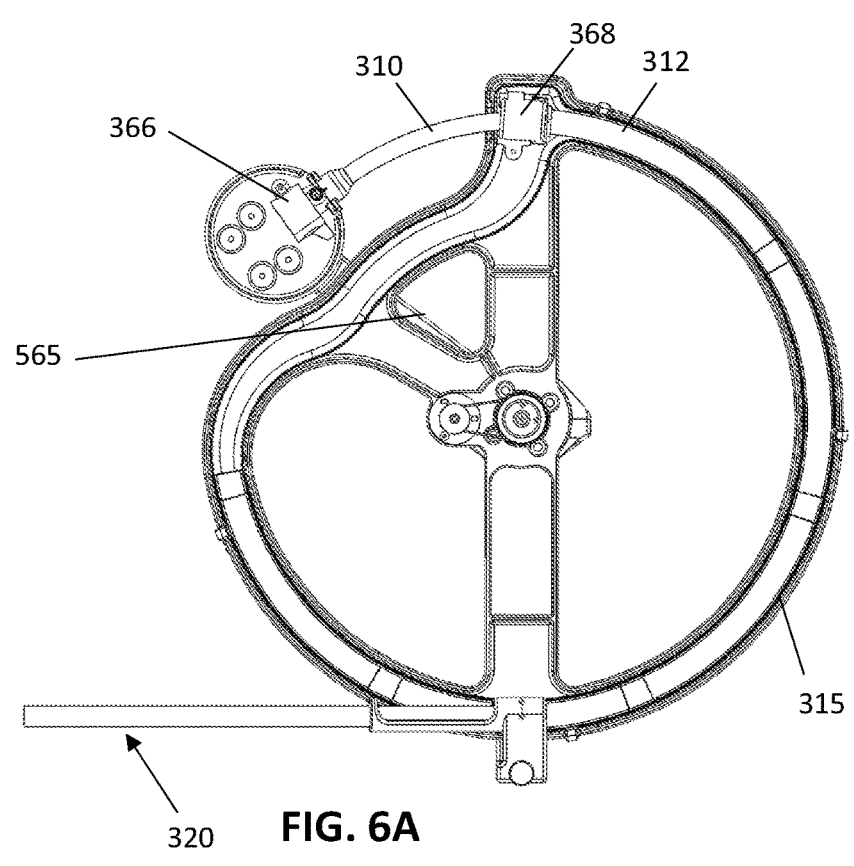
FIGS. 6A-6C illustrate operation of an example of a system for storing and dispensing a robotic scope as described herein.
Figure 6B:
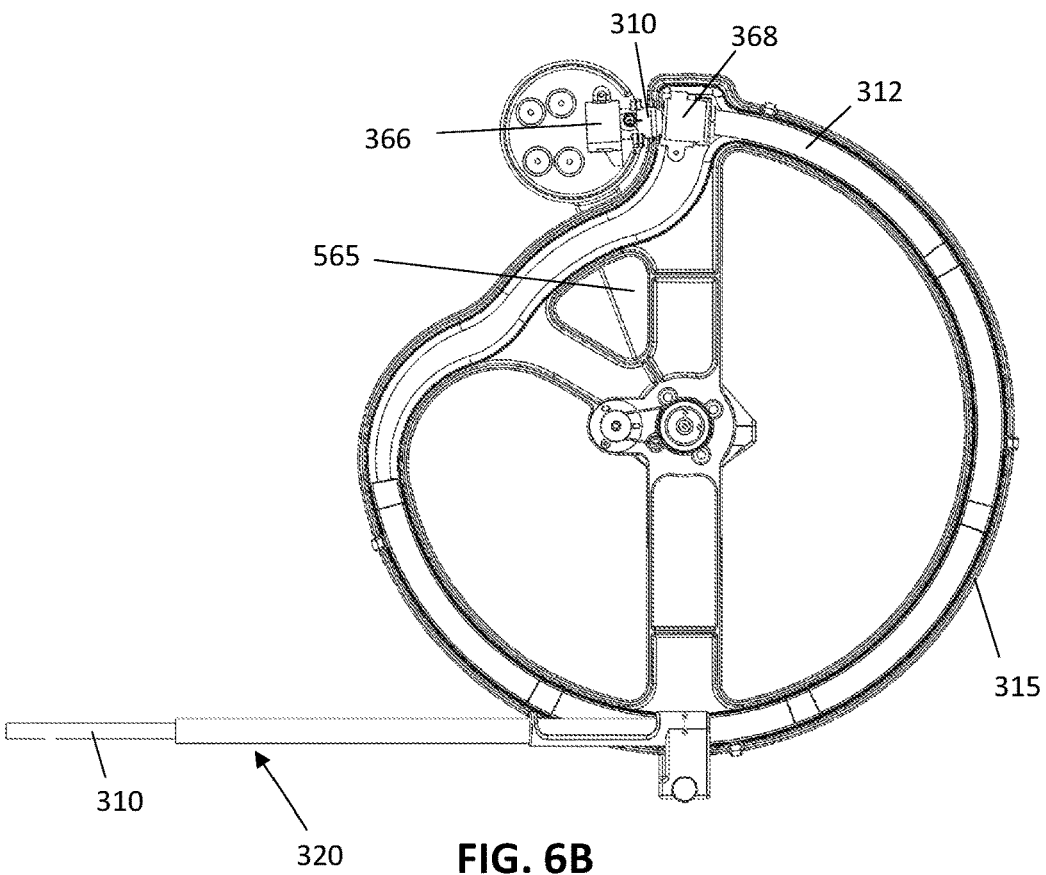
Figure 6C:
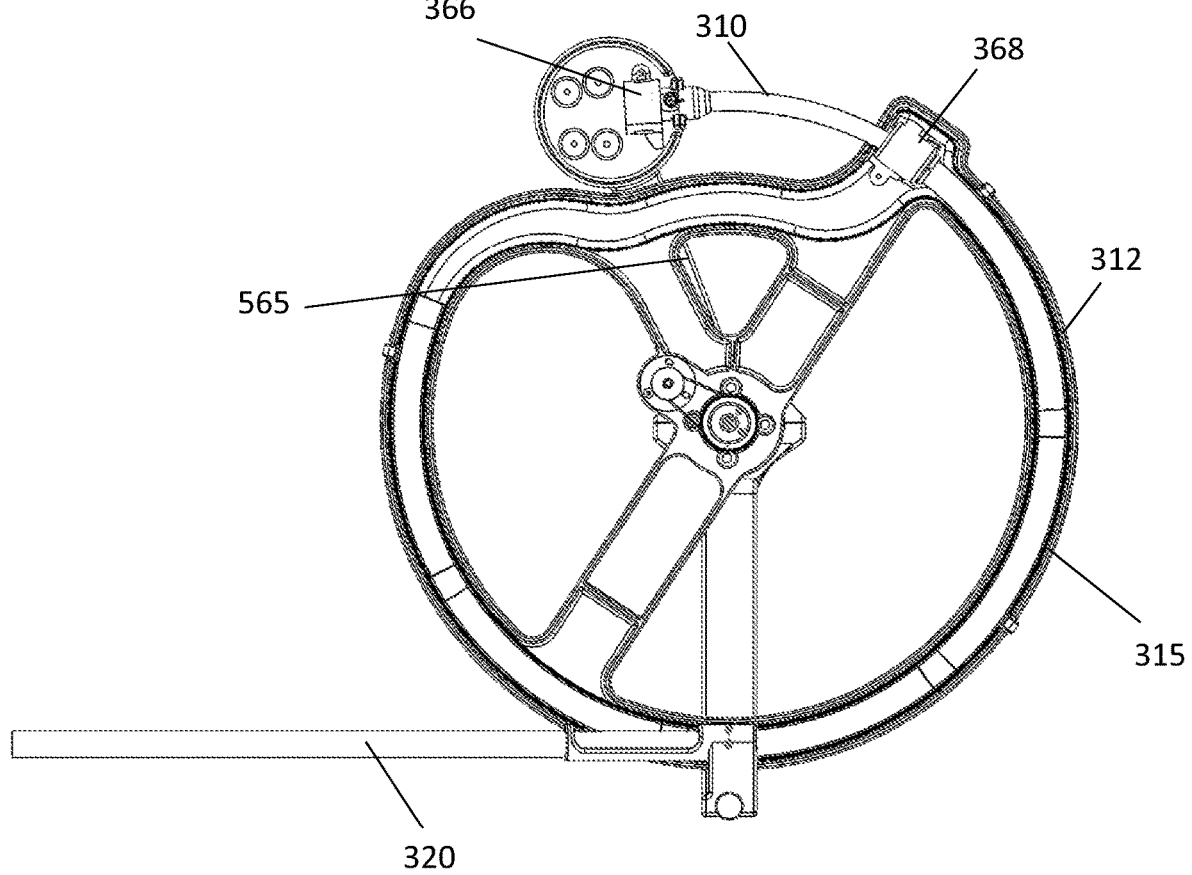

FIGS. 6A-6C illustrate operational positions of the frame 315 at different stages of operation. In FIG. 6A, the inner member (child) is retracted into the outer member (mother), and tip of the inner member 310 is flush with the outer member 312. In FIG. 6B the inner member 310 is extended distally relative to the outer member 312 as shown. This is accomplished by rotating the pivot arm 565 clockwise. In FIG. 6C, the system is shown with the pivot arm in a fixed position (as in FIG. 6B), but with the outer member advanced, e.g., by rotating the frame clockwise. This step may be performed, e.g., as long as the inner member shuttle remains in position. In this example, as the main wheel rotates and outer member may copy the shape of the inner member (e.g., tip shape).

Figure 7:
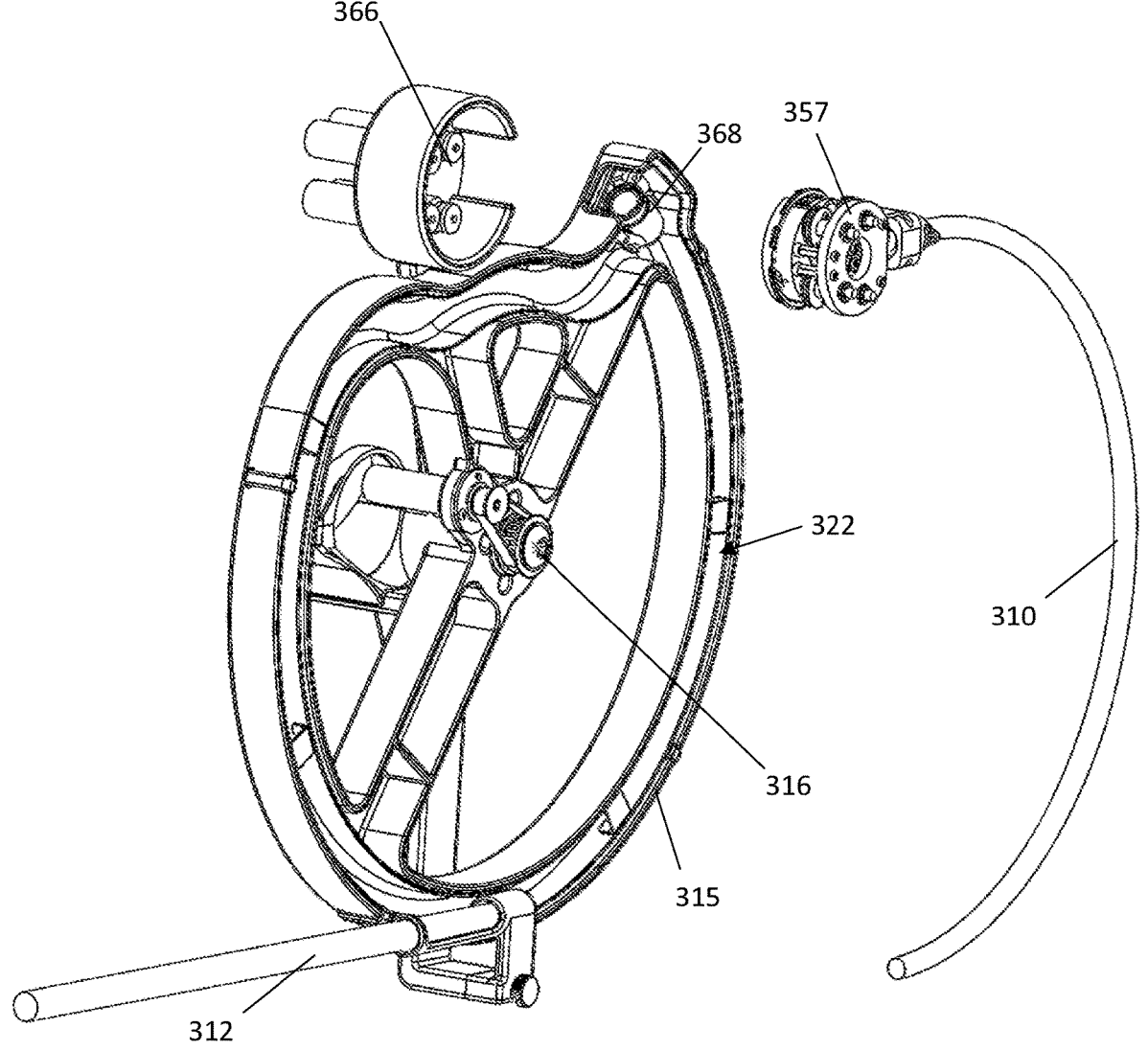
FIG. 7 shows a partially exploded view of one example of a system for storing and dispensing a robotic scope as described herein.
Figure 8:
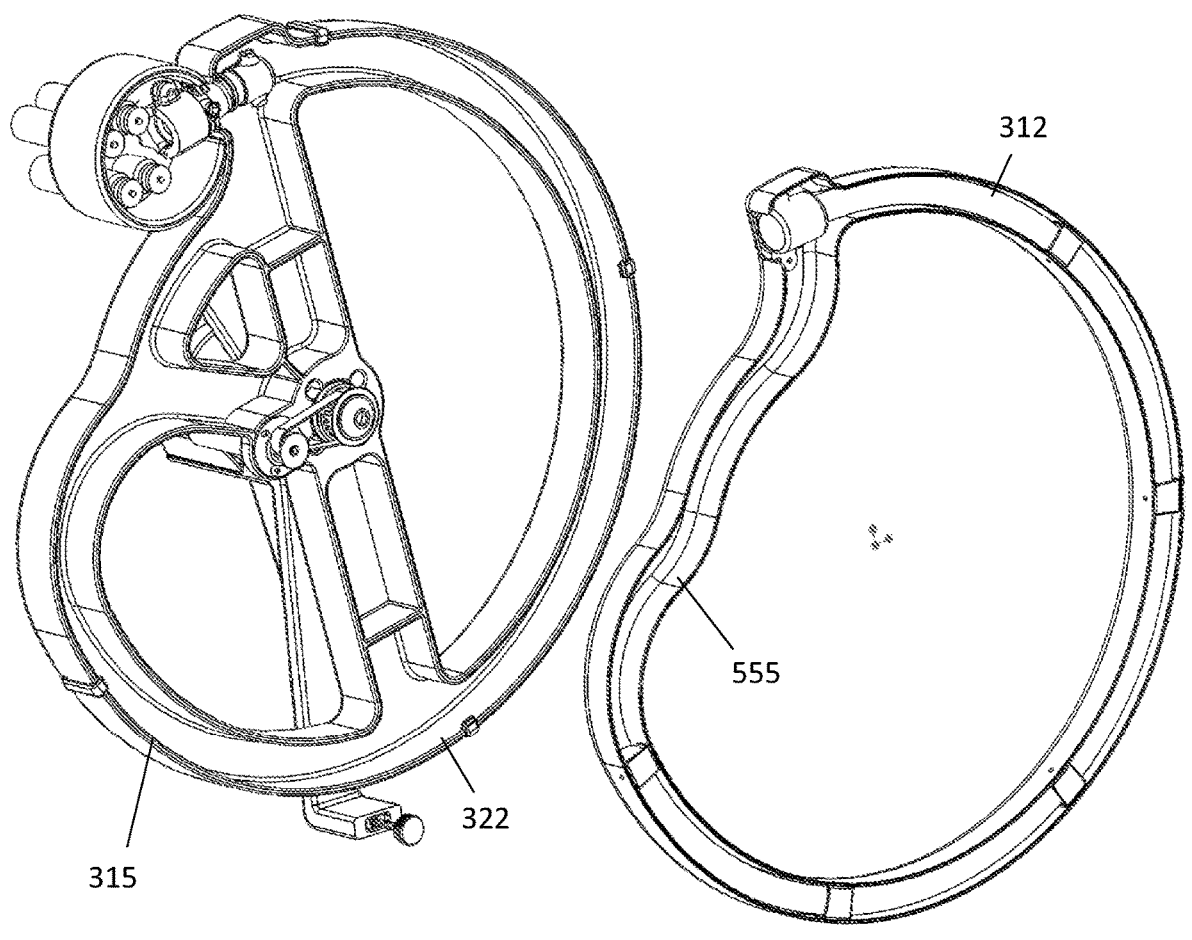
FIG. 8 illustrates an example of a tray and portion of a system for storing and dispensing a robotic scope as described herein.

FIG. 7 shows an example of a partial exploded view of an apparatus similar to that shown in FIGS. 3A-3C, 5A-5C and 6A-6C. In the partial exploded view, the inner member 310 of the robotic scope includes a cassette 357 on the proximal end of the inner member 310. The cassette may engage with the inner member mount 366. The robotic scope may fit directly into the securement 322 of the frame 315, or it may fit into a tray (not shown) that may then be held in the securement 322. For example, the frame may be wheel-shaped and may mate with (via a snap-in connection, etc.) a tray holding the outer member (mother). The tray may be disposable. The inner member may be separate (as shown in FIG. 7) and may be loaded into the inner member mount 366 and through the outer member during setup. For example, FIG. 8 illustrates an example of a frame 315 including a securement 322 into which a tray 555 (that has been pre-loaded with an outer member 312 into the tray securement, e.g., in this example, a channel) may engage. In some examples the tray may snap into the frame and the inner member may be threaded into the pre-loaded outer member.

Figure 9A:
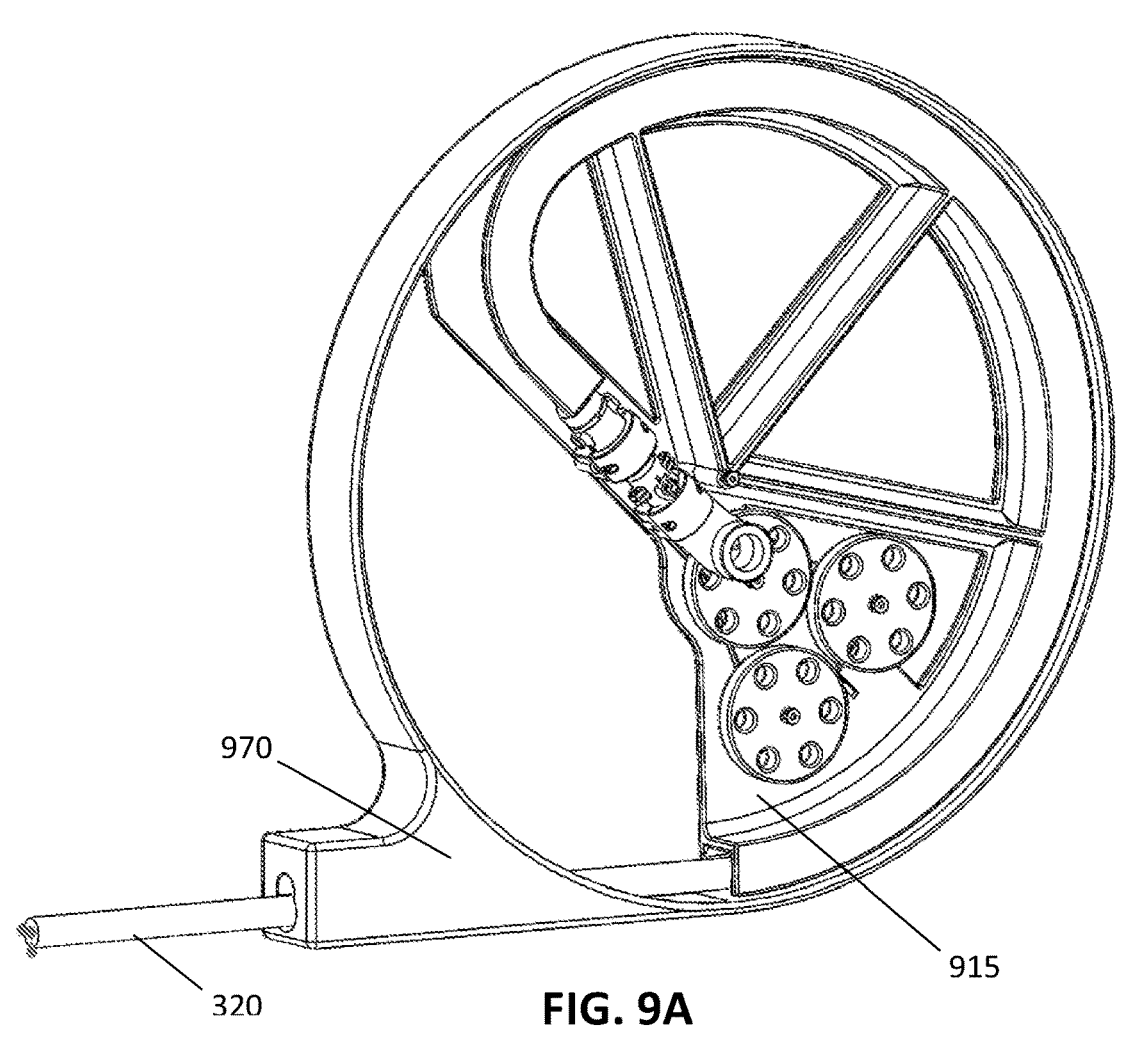
FIGS. 9A-9B schematically illustrate an example of a system for storing and dispensing a robotic scope.
Figure 9B:
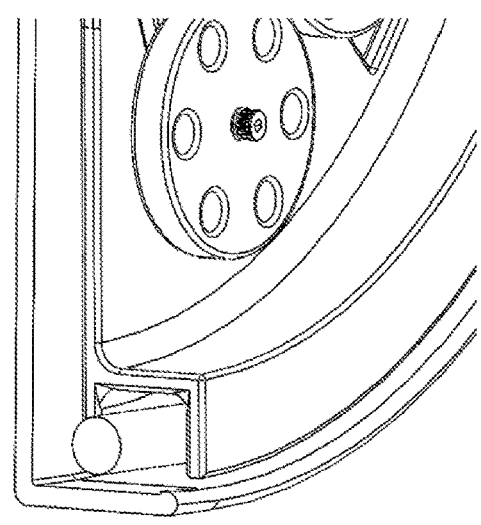
Figure 10A:
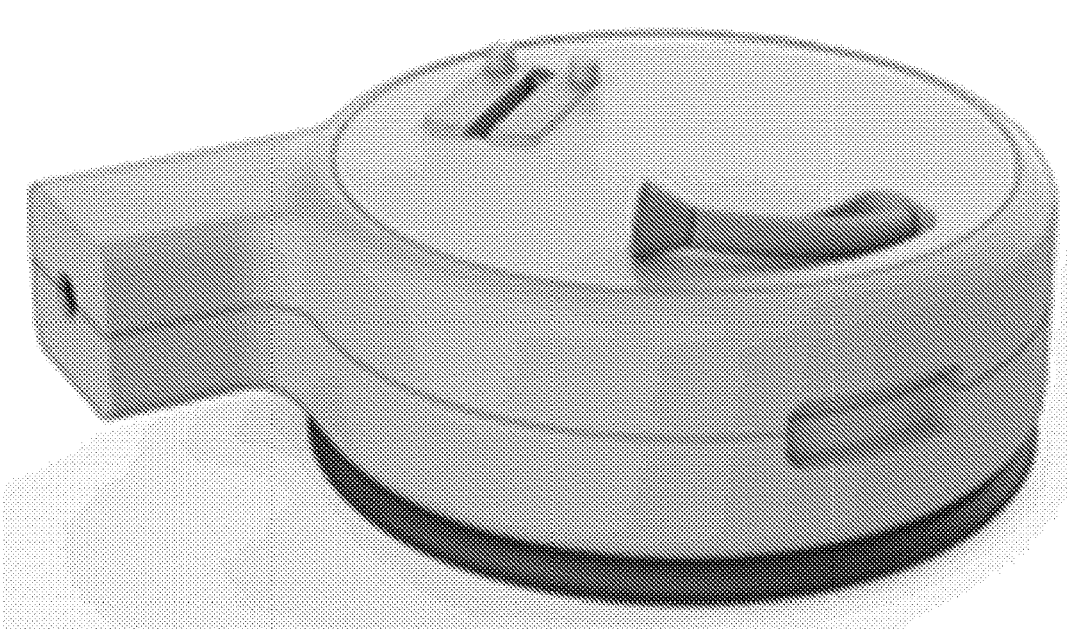
FIGS. 10A-10E schematically illustrate another example of a system for storing and dispensing a robotic scope. This system could be set on the bed. Or it could be attached to another cart with a positioning arm.
Figure 10B:
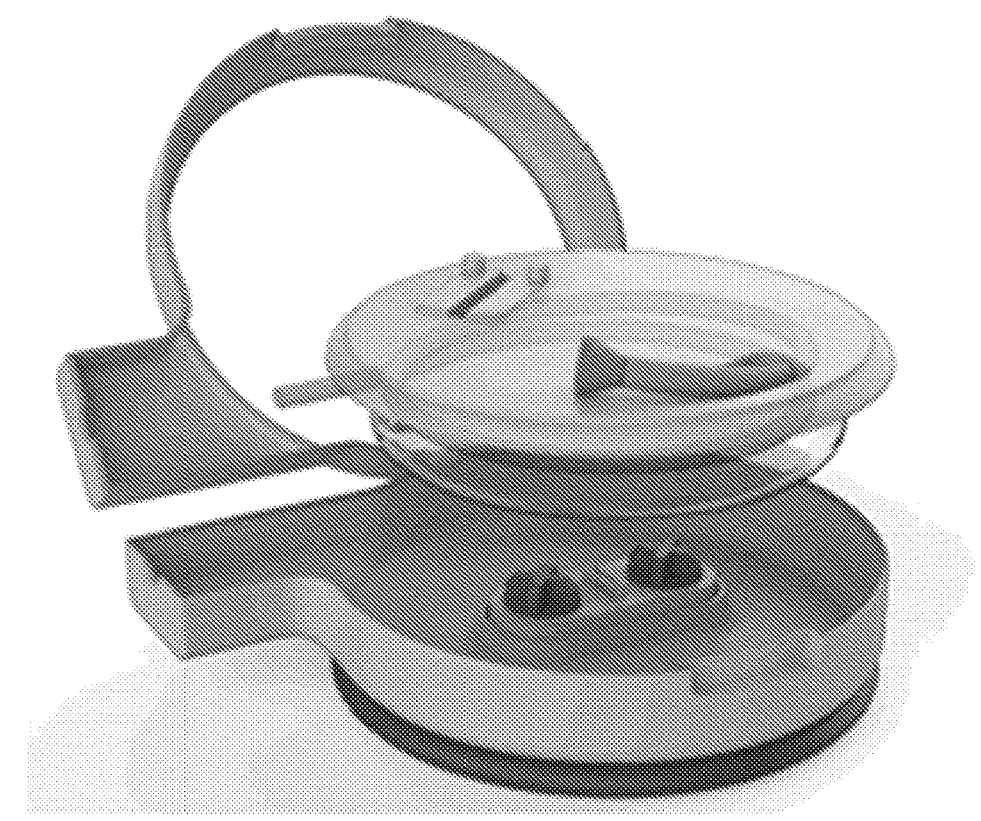
Figure 10C:
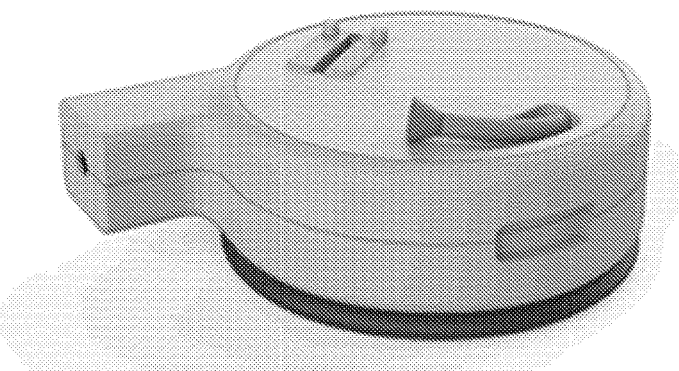
Figure 10D:
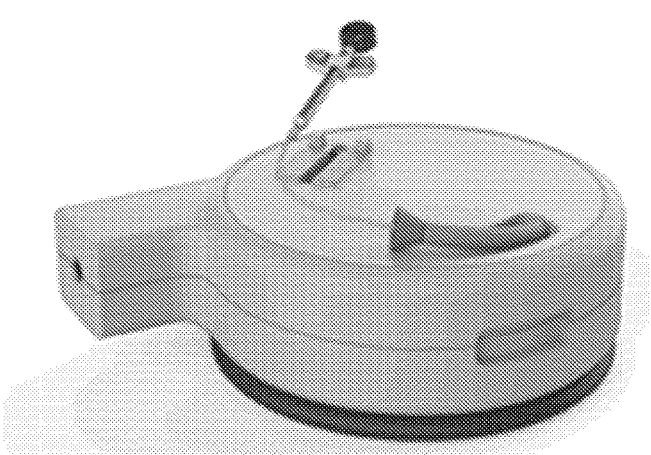
Figure 10E:
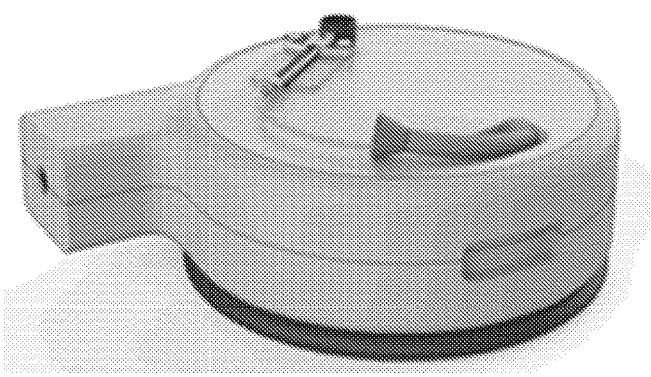
Figures 11A, 11B, 11C, 11D, 11E, 11F:
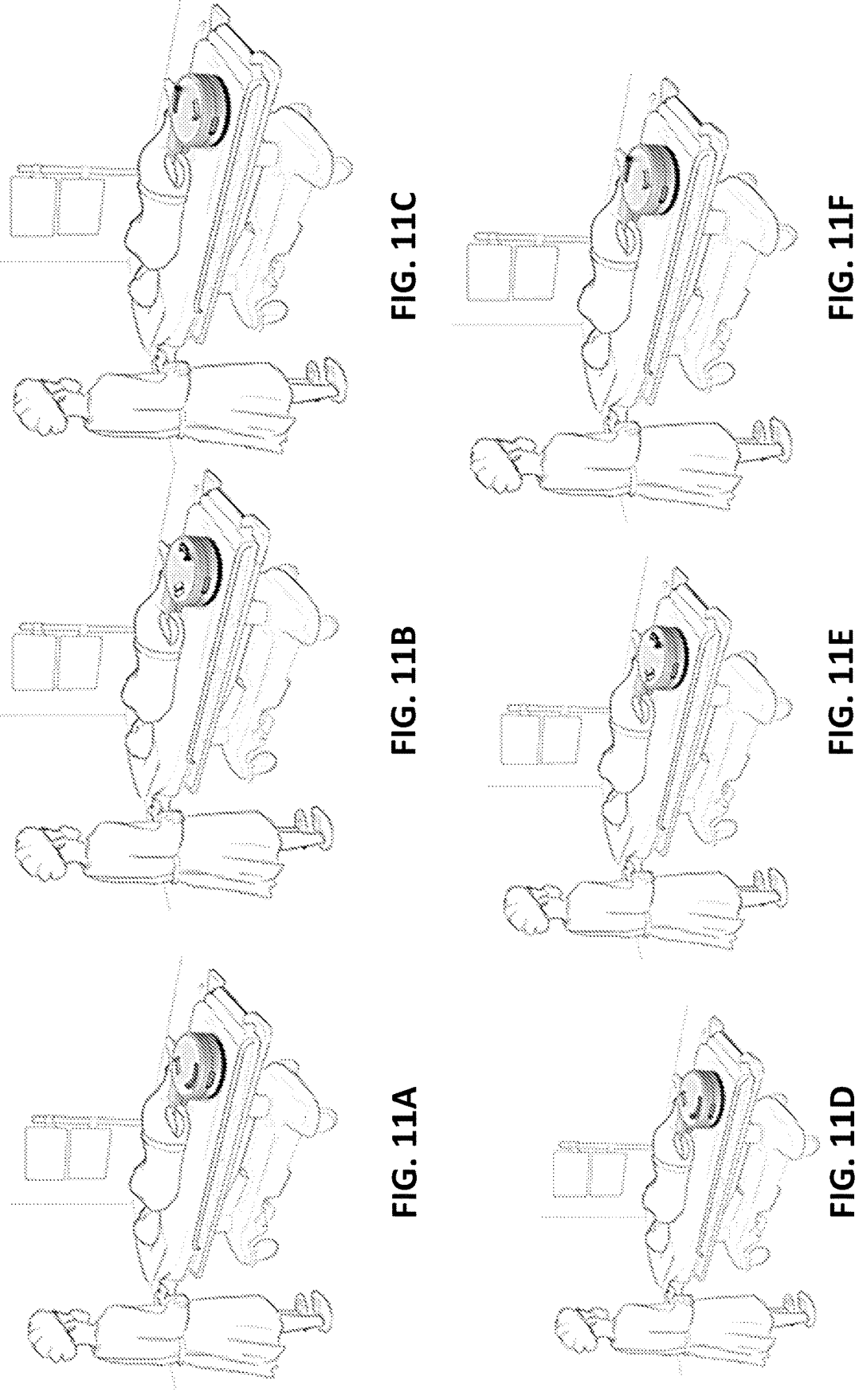
FIGS. 11A-11F schematically illustrate the operation of an apparatus similar to that shown in FIGS. 10A-10E.

FIGS. 9A and 9B illustrate another example of a system including a frame 915 that may rotate relative to an outer housing 970 that has an integrally formed exit guide. Rotation of the frame relative to the outer housing may therefore convert the rotational movement of the frame into a linear extension or retraction of the robotic scope 320.

In use, the apparatus (e.g., system) may be wheeled to the table or bed holding the patient. Leveling/locking casters may be engaged to ensure a stable base for the system. A sterile sheath can be drawn over the lever arm (and inner member shuttle) and robot arm, and the frame may be installed. The robot arm may then be put into 'free run' mode, a mode in which the system may be easily manipulated in a variety of positions and orientations. The robot arm may be manually positioned for loading the two-part rigidizing robotic scope, including the outer member (mother) and inner member (child). A hydrophilic coating (on either the inside of the outer member, the inside of the outer member, or both) may be wetted for activation. The inner member may be inserted into the outer member, and the tray (including the pre-loaded outer member) may be snapped onto the frame. The interface on the inner member may then be coupled into the inner scope mount. The nested mother/child may then be threaded through the system. After loading, the system is positioned near to the patient, and the dual rigidizing endoscopic system is then dispensed as shown in FIGS. 4A-4D.

During use, the system will allow for precise positioning relative to patient, navigation, independent mother and child rigidization, tip articulation, independent mother and child roll, working channels, imaging, illumination, insufflation, irrigation, tip wash and manual and robotic tools. After use, the frame rotates (e.g., ccw/counterclockwise) and the mother and child system may be respooled into the circular tray. The inner member (child) may then be removed from the outer member (mother), and the tray, mother, and disposable elements of the child (fluid lines and working channel) may be discarded. The frame may be uninstalled and cleaned in a washing system, or other appropriate method. The sterile sheath may be removed from the robot arm and discarded.

As described above, these apparatuses may reduce the form factor and space requirements for using a long length catheter or endoscope in the medical suite. Straight line dispensing is also a viable option, but it would require the full length of the endoscope to be available at the foot of the patient bed (see, e.g., FIGS. 12A-21E, below). Curved or angled or arc-shaped systems such as those described herein may partially reduce length. With a rotary dispense design, the space required is greatly reduced. Further, handling and mounting are simplified, as the swappable components may be in a smaller form factor stored in a removable cartridge. This configuration may be used with a large number of different systems, including existing systems, and is adaptable to multiple patient sizes, positions, and orientations.

The apparatus may be used with tools. For example, tools and entry point may be positioned at an accessible height for people. This position is stable and does not move much during the procedure. Further, these apparatuses are generally easy to load and transfer from the packaging. The components may be easily stored (e.g., during shipping and afterwards) and may be used without impeding loading or unloading of the inner member. The reusable elements are easy to clean, not too expensive, and not too large (e.g., may fit in sterilization chamber).

Although the example shown in FIGS. 3-9B include a robotic arm as part of the drive system, in some examples, a compact, bed-top variation is shown. In this example, illustrated in FIGS. 10A-10E and FIGS. 11A-11F, the apparatus may be stored and dispensed from a housing in which the robotic scope is housed. To top of the apparatus may be couped to the rotating frame, and may rotate relative to the base, as shown in FIGS. 10C-10D and 11A-11F.

Also described herein are drive systems including one or more linear drive systems that may be used with any of the rotatable (e.g., wheel-shaped) frames described herein or may be used separately for loading, dispensing or deployment, driving (e.g., advancing/retracting, steering, etc.), and/or withdrawing one or more endoscopes, catheters, overtubes and/or guidewires, and in particular long-length endoscopes, including colonoscopes and enteroscopes as described herein. As with any of the embodiments above, these methods and apparatuses may be adapted for use with a nested (e.g., concentric) elongate tools (e.g., scopes, sheathes, etc.), including but not limited to those having an outer scope member (e.g., outer rigidizing member) and an inner scope member (e.g., inner rigidizing member).

Figure 12B:
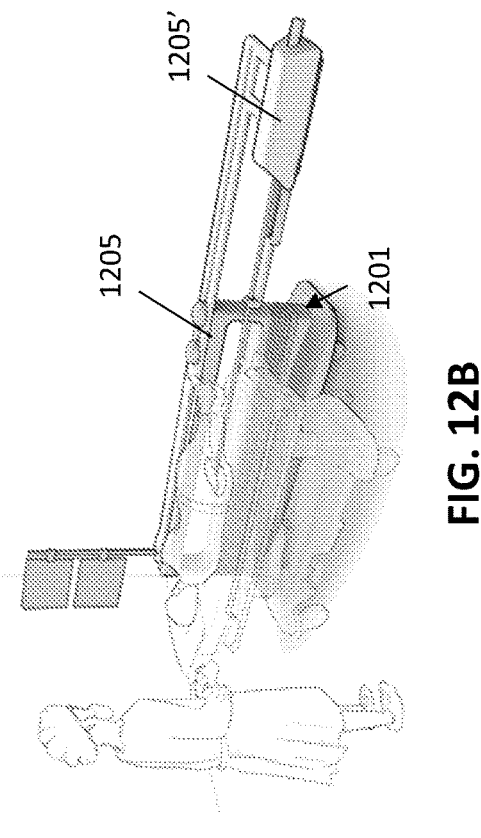
FIGS. 12A-12D schematically illustrate an example of a linear system for dispensing a robotic scope, configured as a rail and cart system having no turns or bends.
Figure 12D:
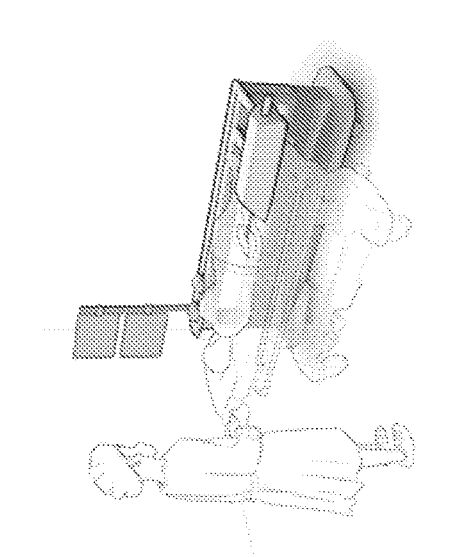
Figure 12A:
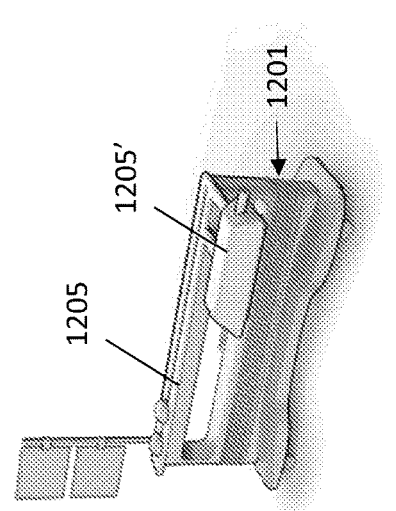
Figure 12C:
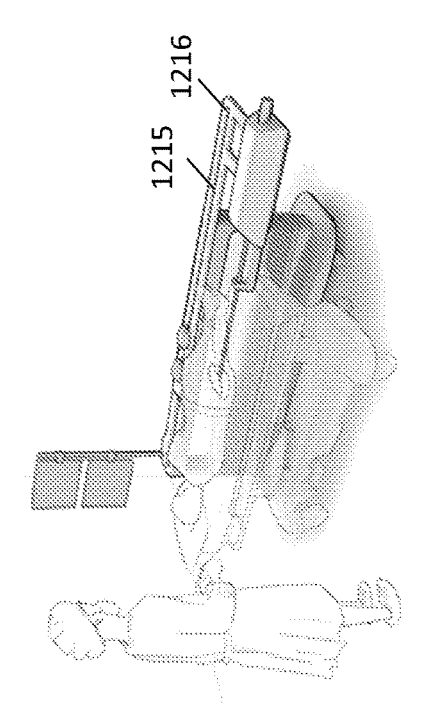

For example, FIGS. 12A-12D illustrate one example of a drive apparatus (e.g., drive system) that may be used with a scope, and in particular with a plurality of nested scopes, as described herein. In FIG. 12A the apparatus includes a base 1201 that may be configured to be mobile (e.g., including wheels, etc.) but may lock securely in place and may be configured to prevent tipping. The base may include one more linear drives 1205. The linear drive may be part of and/or coupled to the base region and may include one or more actuators to move in/out (in a proximal to distal direction) relative to the base. The linear drive may couple with a frame (e.g., a frame that may be removable) that may couple with a holder for an endoscope or endoscopes, including nested pair of scopes. In FIG. 12A the holder or frame includes an outer cover covering a second linear drive 1205' that may move in/out relative to the first linear drive and may be coupled to, e.g., an inner scope (e.g., inner member such as an inner rigidizing member) to drive independent movement of the inner member relative to the outer member. The outer member may be coupled to the liner driver. FIG. 12B shows the example of FIG. 12A with the first linear drive 1205 activated to extend the frame holding the frame covering the nested scope and the second linear drive 1205'. In FIGS. 12B-12D a patient is also shown, and the scope (e.g., nested colonoscope) includes a nested pair comprising an inner member and an outer member that are independently controlled by the first and second linear drives. The first linear driver may move the outer and inner member together. The second linear driver may move just the inner member. Movement of just the outer member relative to the inner member may be achieved by moving the inner member (actuating the second linear drive) in a direction that is opposite to the direction of movement of the outer member.

In FIGS. 12A-12D the linear drivers 1205, 1205' are configured to move an attached outer and inner member, respectively, in a linear direction relative to the patient (e.g., in/out, proximal/distal). Either or both the first and second linear drives may also be configured to rotate the outer and inner members to which they are attached. In the example shown in FIGS. 12A-12D the second linear drier is moved by the first linear driver. The first linear driver includes a pair of parallel support arms 1215, 1216 that are rigidly connected to each other and to a platform that supports the second linear driver. The support arms are moved by the first linear driver to move the platform (e.g., in/out, proximal/distal). The second linear driver includes a second arm or set of arms that are driven by the second linear driver to move an attached inner member (e.g., in/out, proximal/distal). The outer member may be coupled to the support platform and the inner member may be coupled to the second arm or sets of arms.

Figures 13A, 13B, 13C:
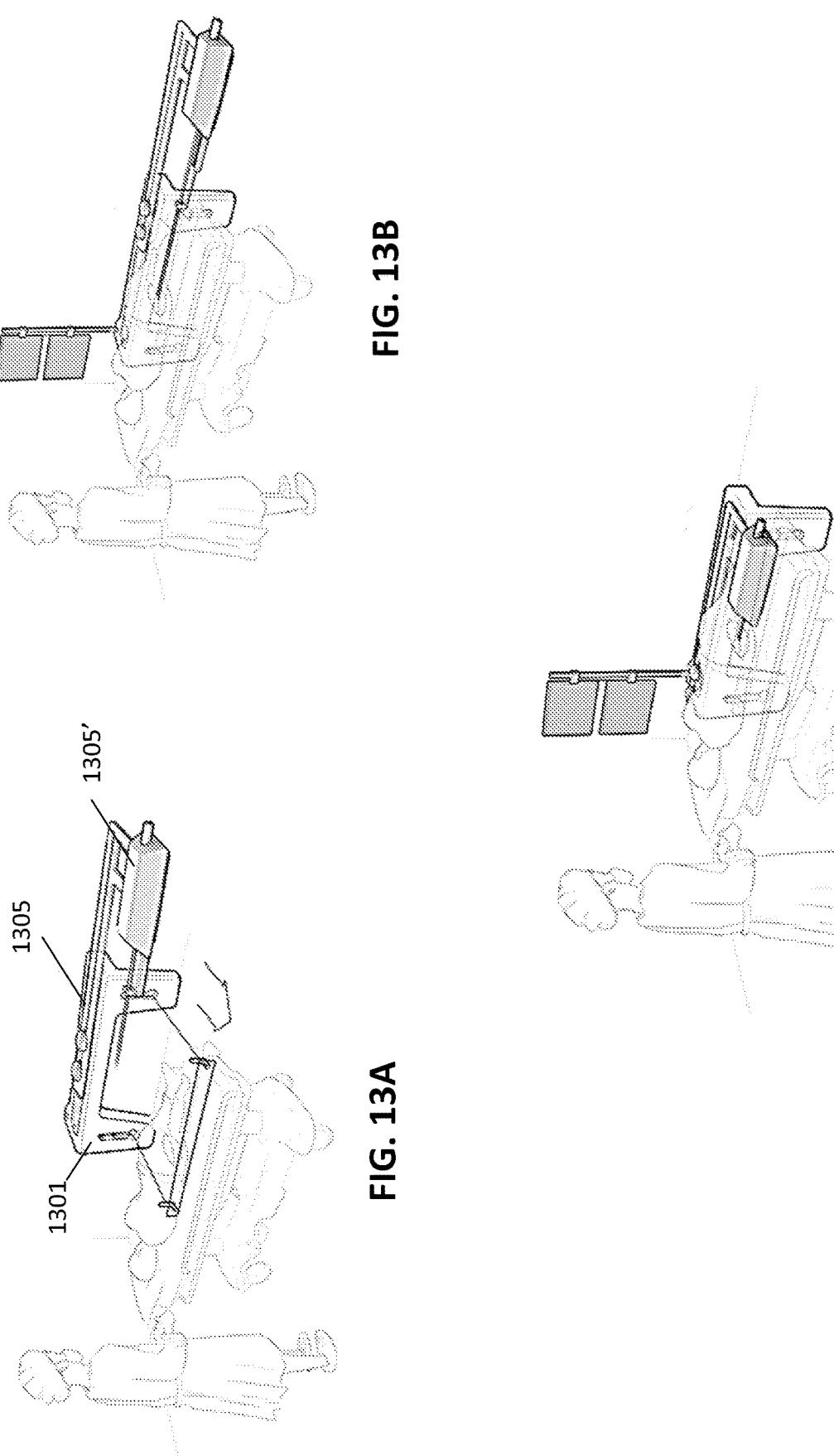
FIGS. 13A-13C schematically illustrate an example of a linear system for dispensing a robotic scope, configured as a rail and gurney system having no turns or bends.

FIGS. 13A-13C illustrate another variation of a drive system similar to that shown in FIGS. 12A-12D. In FIGS. 13A-13C the drive system is not freestanding as in FIGS. 12A-12D, but is mounted to a bed. For example, in FIGS. 13A-13C the first 1305 and second 1305' linear actuators are coupled to a mounting base 1301 that couples to the patient bed, as shown in FIG. 13A. Once mounted, the system may operate similar to the system of FIGS. 12A-12D. The system of FIG. 13A-13C may mount in any appropriate manner, including by bolting, clamping, etc. Once mounted, the system may be rigidly coupled to the bed (e.g., bedframe). The system may be later removed and mounted to another bed/bedframe.

FIGS. 14A-14D illustrate an example of a drive system including a freestanding base 1401, and a robotic arm 1405 to which a linear drive 1405' is connected. The robotic arm may move the linear drive in six or more degrees of freedom. The linear drive 1405', similar or identical to the second linear drive of FIGS. 12A-12D and 13A-13C, may include one or more arms that move in a line (e.g., in/out, proximal distal). A nested device having an inner member moveably nested within an outer member, as described above (including in particular any of the rigidizing robotic members described above), may be coupled to the drive system so that the inner member is coupled to the one or more arms moved by the linear drive 1405' and the outer member is coupled so as to move with the robotic arm 1405. For example, the outer member may be coupled to the non-moving portions of the linear drive 1405' or to the platform on which the linear drive is attached. As mentioned above, the drive system may also include roll actuators to rotate the inner and/or outer members in their long axes (e.g., in roll).

In any of the drive systems described herein, the drive system may also be configured to include or allow rigidization control of the inner and/or outer members. For example, in pressure rigidizing systems the drive systems may include one or more pressure lines (e.g., positive pressure and/or negative pressure) and/or a pressure manifold for controlling applying pressure to an inner and/or outer member that are attached to the drive system. Any of these apparatuses may also be configured to allow angulation (steering) of the inner and/or outer members, including steering the distal end regions. For example, the drive system may include one or more motors (and corresponding control sub-systems) for actuating steering of the inner and/or outer members. In some examples, the drive system may include one or more motors that actuate steering members (e.g., tendons, lines, wires, etc.) to controllably bend the distal tip region of either the inner and/or outer members.

In FIGS. 14A-14D, the base may include wheels that may be locked in position to secure the drive system relative to a patient and bed. The base may be weighted and may be configured to distribute the weight over a relatively large area to prevent tipping of the drive system during operation even where the robotic arm is extended fully away from the midline of the base. FIGS. 14B-14D show an example of a bed on which a patient 1450 is lying positioned next to the drive system; the robotic arm may be actuated to move the nested inner and outer member relative to the patient, and the liner drive 1405' coupled to the robotic arm 1405 may be actuated to move the inner member relative to the patient.

Figures 15A, 15B, 15C:
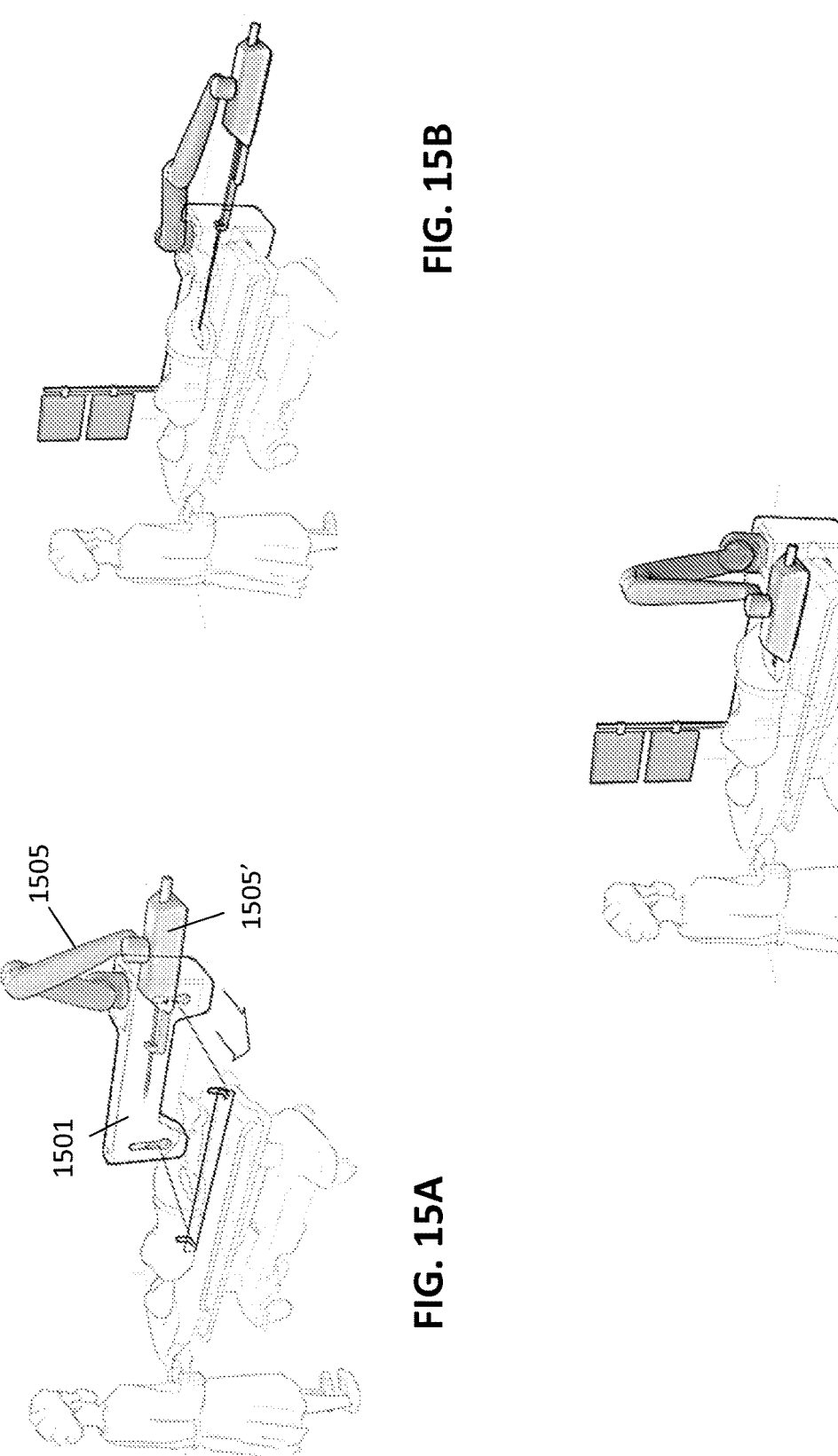
FIGS. 15A-15C schematically illustrate an example of a linear system for dispensing a robotic scope having a robot arm on a gantry.

FIGS. 15A-15C illustrate another variation of a drive system similar to that shown in FIGS. 14A-14D. In FIGS. 15A-15C the drive system is not freestanding as in FIGS. 14A-14D, but is mounted to a bed (e.g., bedframe). For example, in FIGS. 15A-15C the robotic arm 1505 and linear actuator 1305' are coupled to a mounting base 1501 that couples to the patient bed, as shown in FIG. 15A. Once mounted, the system may operate similar to the system of FIGS. 14A-14D. The system of FIG. 15A-15C may mount in any appropriate manner, including by bolting, clamping, etc. Once mounted, the system may be rigidly coupled to the bed (e.g., bedframe). The system may be later removed and mounted to another bed/bedframe.

In some examples the drive system may include multiple drives (e.g., robotic arms, linear actuators, etc.) that are separately mounted. For example, FIGS. 16A-16E illustrate an example of a drive system including a first base 1601 to which a first robotic arm 1605 is coupled, and a second base 1601', to which a second robotic arm 1605' is coupled. The second base in this example may be rigidly mounted to a wall or ceiling, as shown. Alternatively in some examples the second base may be floor-mounted or may be movable (e.g., rolling, etc.). The first base may be mounted to the floor or may be a rolling or movable base. In operation the first base and the second base may be locked in position relative to each other. In FIGS. 16A-16E the nested scope apparatus may be coupled to the second robotic arm 1605'; in some examples the second robotic arm may also include a linear actuator coupled to the arm to drive movement of the inner member relative to the outer member. The first arm may include a guide 1609 (e.g., mount, loop, etc.) that may help control the position of the elongate nested apparatus in space relative to the patient. For example, in FIG. 16A the system may control, via a drive system controller, which may be separate from or part of the overall system controller, the first robotic arm and the second robotic arm; the system may map the location of patient, including patient anatomy. For example, the system may be told and/or may determine the position of the patient's anus and may use this position to determine movement of the robotic arms (and/or linear actuator).

Figures 16A, 16B, 16C, 16D, 16E:
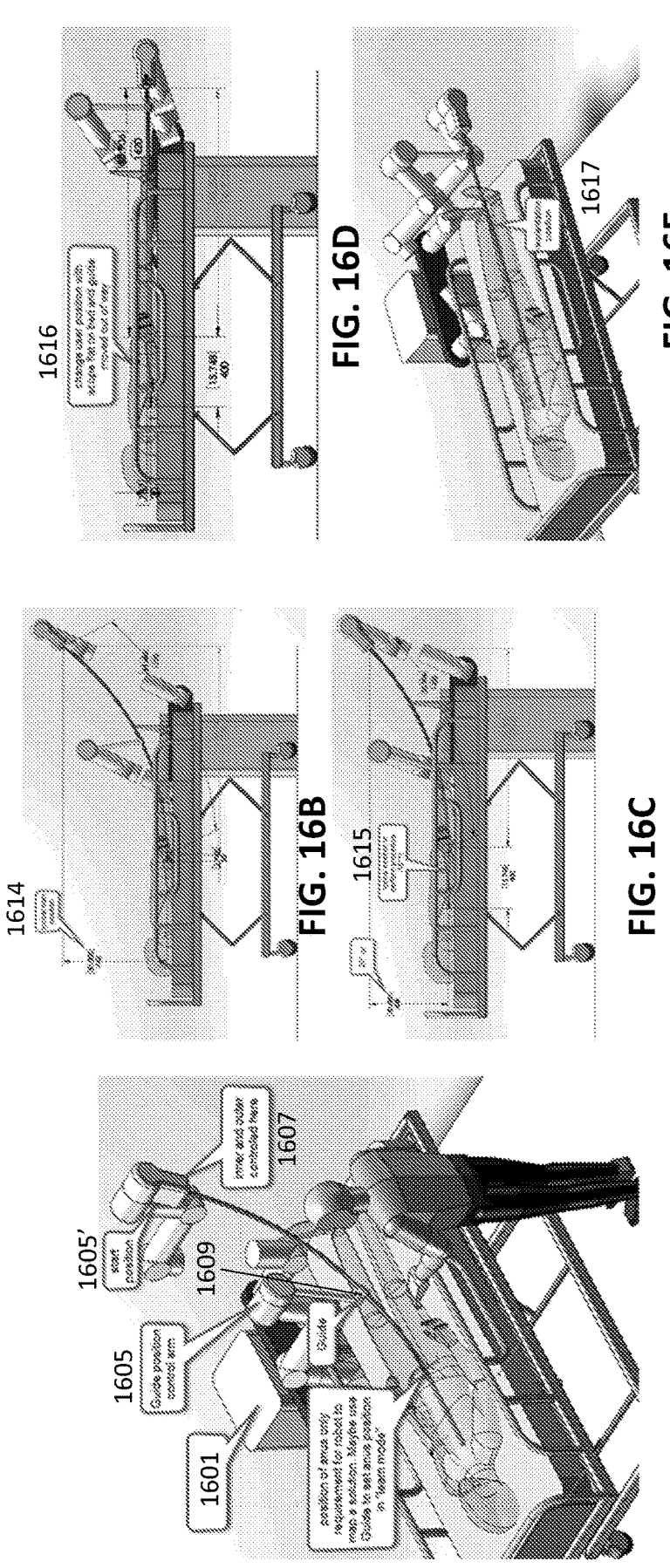
FIGS. 16A-16E schematically illustrate an example of a linear system for dispensing a robotic scope having a turn towards a vertical orientation (e.g., up to a 90 degree or more turn) and a robot arm.

In operation, as illustrated in FIGS. 16B-16E, the system may coordinate the movement of the robotic arms and/or any linear actuator to insert and control relative position between the patient and the scope(s). the first robotic arm may be manipulated to control the region of the scope as it approaches the patient. Both the first and second robotic arms may be positioned over the patient by a relative distance 1614 after starting the procedure, including moving the one or more arms to a typical position to start the procedure 1615. The system may include one or more modes in which the robotic arms position the system out of the way of the medical staff (e.g., doctors, nurses, etc.), as shown in FIG. 16D. In some examples, the system may be configured to move the robotic arms out of the way of the medical staff while performing the procedure, as illustrated in FIG. 16E. The system may move the first and second robotic arms to a reorientation position 1617 in which the patient position may be changed without risking damage or harm to the patient.

Figure 17E:
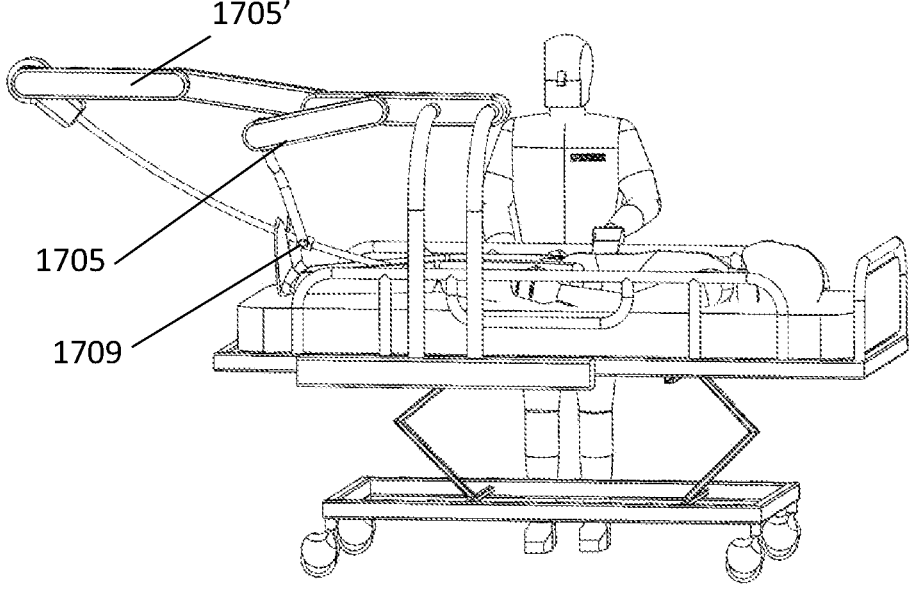

FIGS. 17A-17E illustrate another example of a drive system including multiple linkages 1704 slowing positioning of the attached endoscope, e.g., nested endoscopes, to be inserted and/or withdrawn from the patient. In FIG. 17A the drive system is shown coupled to the patient bed, in a start position. The drive system includes a first arm 1705 coupled to a guide 1709 (similar to the example shown in FIGS. 16A-16D) that is movably attached to the endoscope (e.g., nested endoscope 1740) shown inserted into the patient. A second arm 1705' extends more distally from the patient, but has a larger range of movement, and may also include a liner actuator, e.g., for advancing and/or retracting the inner member of the pair of nested members. The outer member may be coupled to the second arm; the first arm and the guide may help position and orient the endoscope as it is moved relative to the patient. FIGS. 17B-17E show different views of the endoscope and drive system in use.

Figures 18A, 18B, 18C:
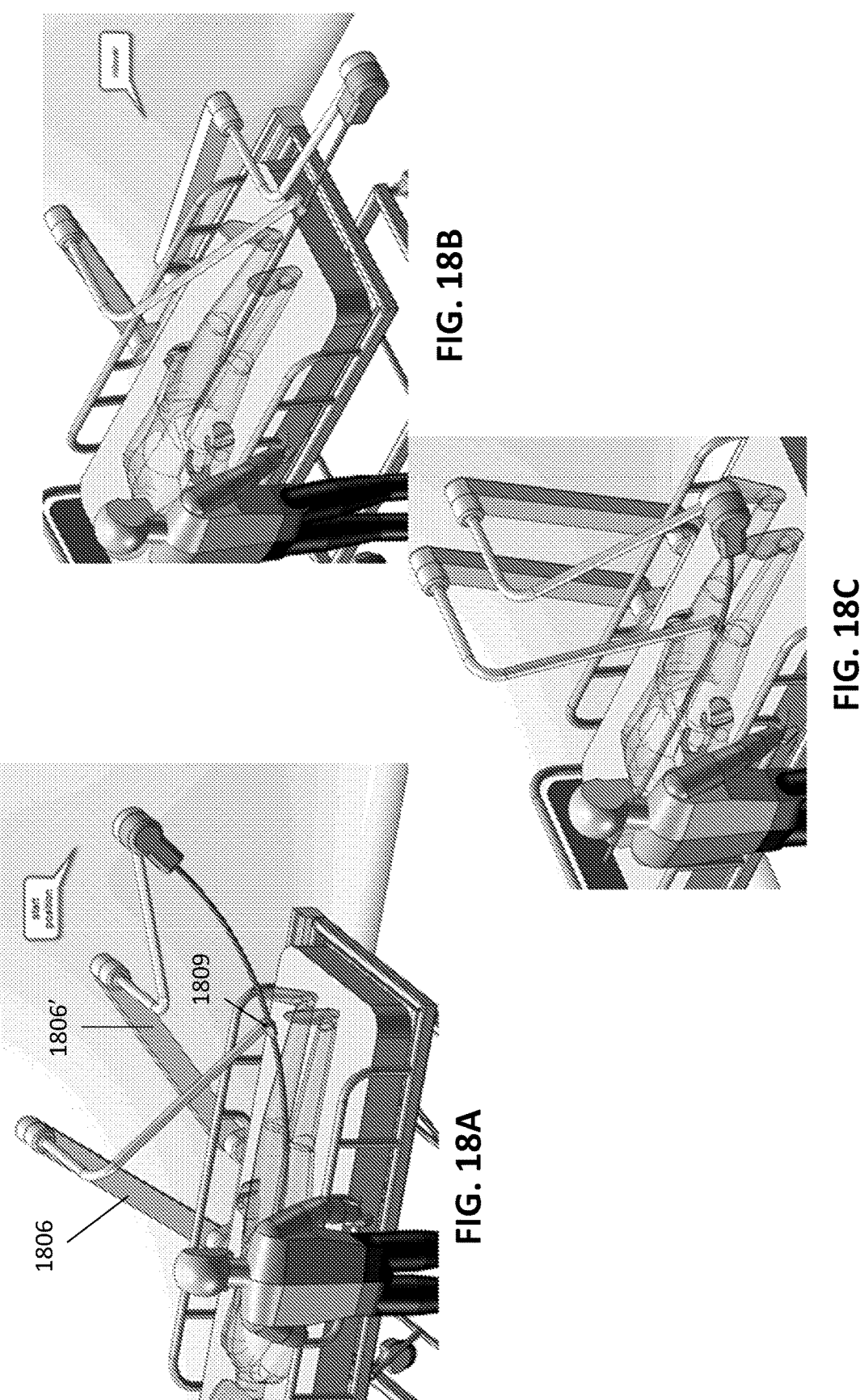
FIGS. 18A-18C schematically illustrate an example of a linear system for dispensing a robotic scope having a turn towards a vertical orientation (e.g., up to 90 degree or more turn), and a pair of bed-mounted robot arms.

FIGS. 18A-18C illustrate an example of a drive system that is mounted to the bed, similar to FIGS. 17A-17E, and also includes a pair of drive arms. The first drive arm 1806 includes a guide 1809 similar to that shown in FIGS. 16A-16E and 17A-17E. The second drive arm 1806' is coupled to the endoscope, e.g., nested endoscope. In this example, the second drive arm may also include a linear actuator for moving the inner member of the nested endoscope relative to the outer member. FIG. 18A shows the drive system in a start position. FIGS. 18B and 18 show operational positions of the first and second drive arms. In this example, as in FIGS. 16A-16E and 17A-17E the drive system approaches the patient from a position that is elevated relative to the body of the patient being treated.

Figure 19:
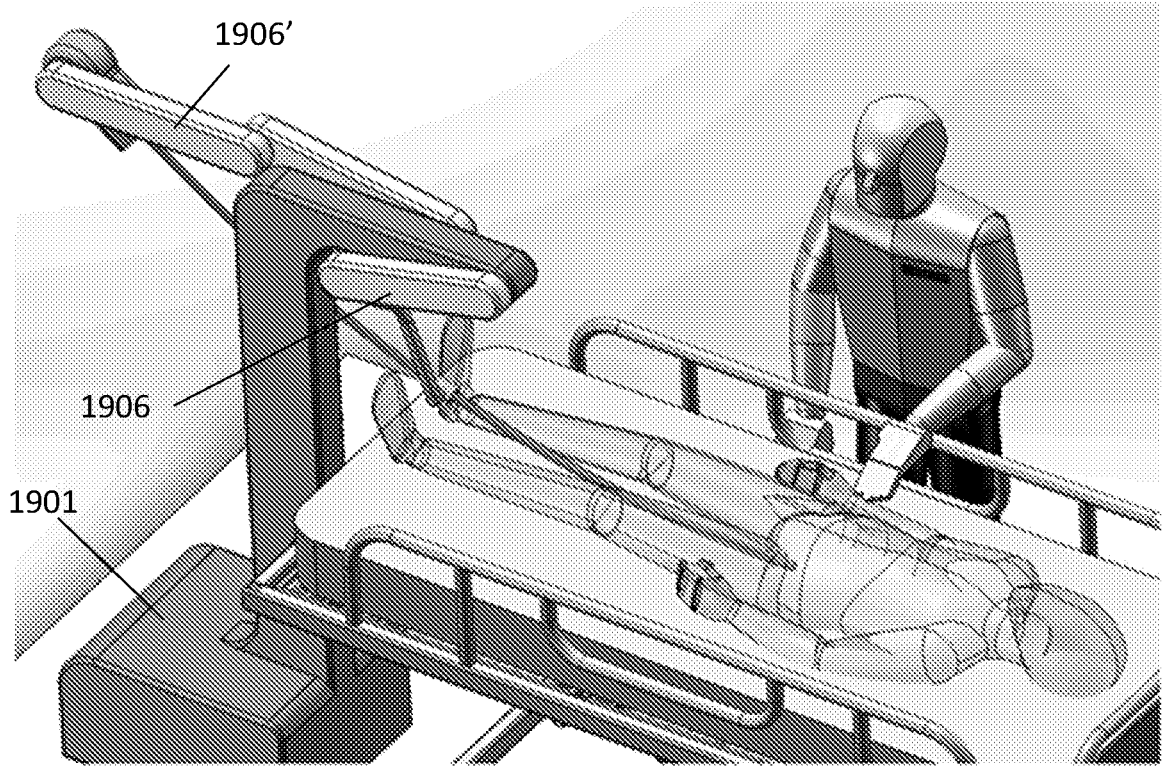
FIG. 19 schematically illustrate an example of a linear system for dispensing a robotic scope having a turn towards a vertical orientation (e.g., up to 90 degree or more turn).
Figures 20A, 20B, 20C, 20D, 20E, 20F:
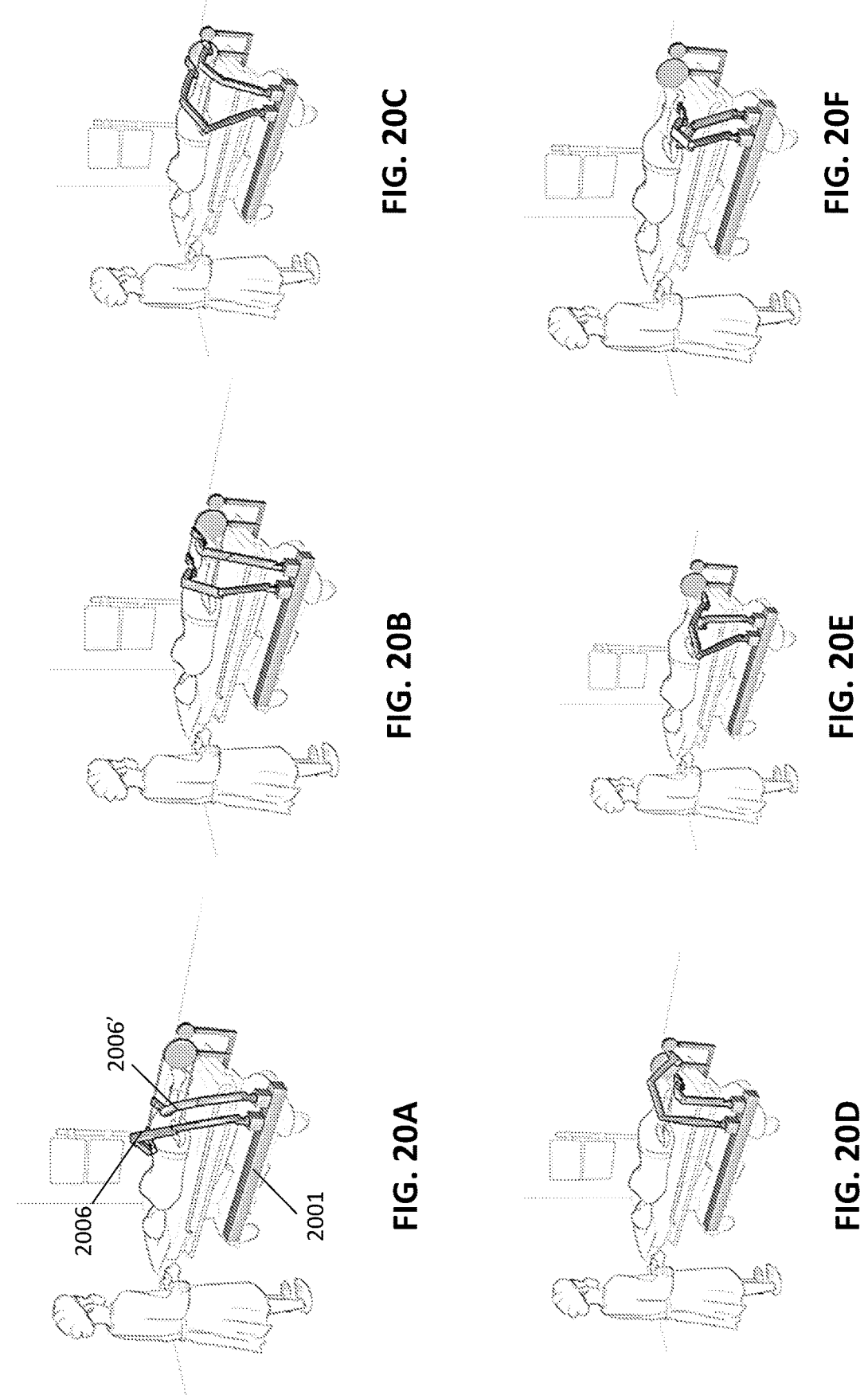
FIGS. 20A-20F schematically illustrate an example of a linear system for dispensing a robotic scope having a 180 degree turn and two robot arms.
Figures 21A, 21B, 21C, 21D, 21E:
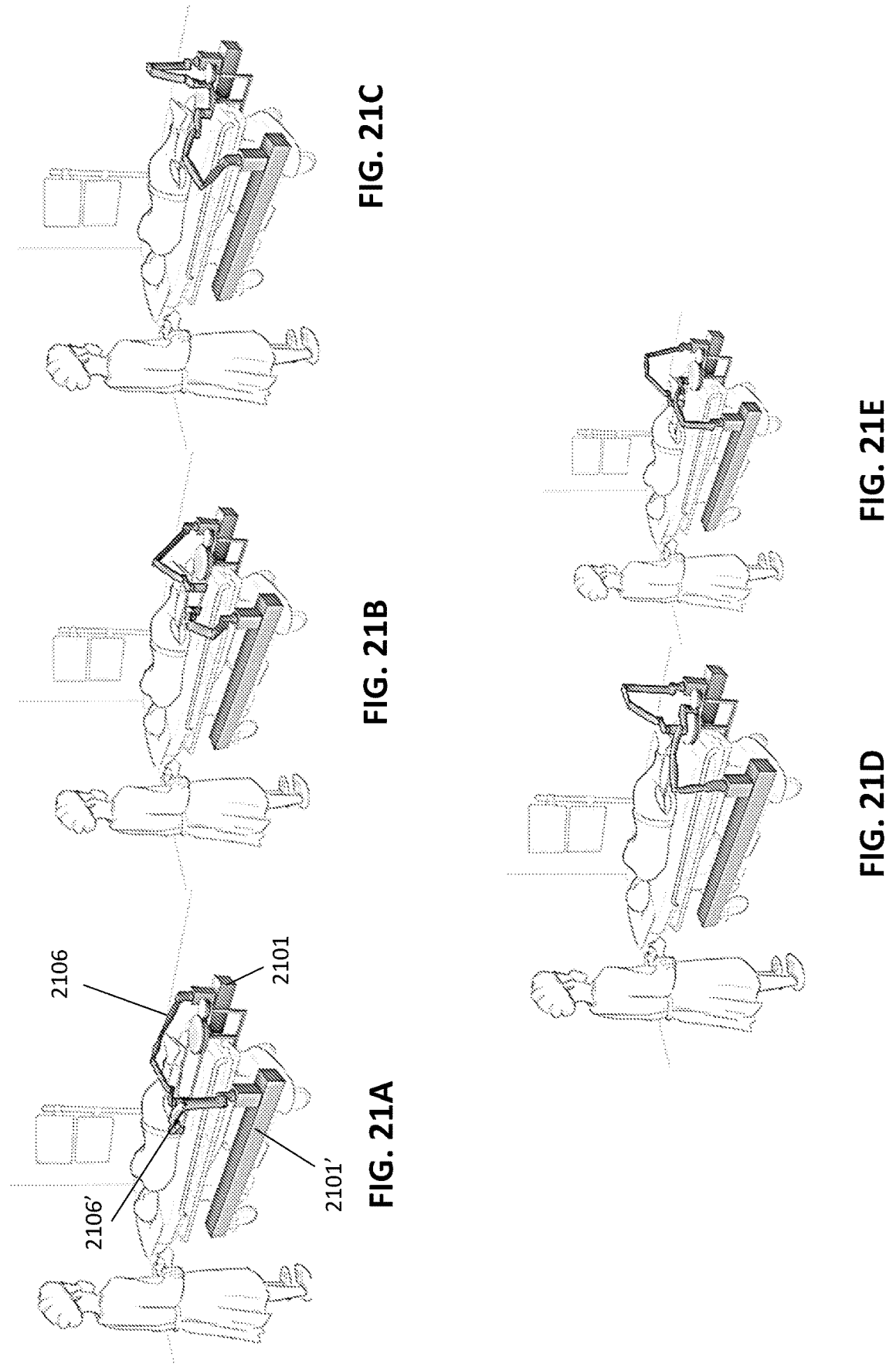
FIGS. 21A-21E schematically illustrate an example of a linear system for dispensing a robotic scope having a 180 degree turn and tow robot arms.

FIG. 19 shows an example of a drive system in which the system is configured to be positioned at the foot of the patient's bed, rather than by the side of the patient's bed. The drive system in this example includes a base 1901 that may be moveable and may lock in position. In this example two multi-linkage drive arms 1906, 1906' extend up from the base; one of the arms may include a guide 1909 that may help control the position of a catheter (e.g., a nested catheter), while the second drive arm may couple to the catheter. In some examples a linear actuator may be coupled to the second arm and may drive the movement of the inner member of the nested catheter.

FIGS. 20A-20F illustrate an example of a drive system that is configured to be positioned below the patient's bed and may extend one or more arms up to control movement of the catheter (e.g., nested catheter). For example, in FIG. 20A the drive system include a base 2001 that is positioned near the ground, and below the patient's bed, as shown. A first robotic arm 2006, and a second robotic arm 2006' extend up from the base and move relative to the patient to control movement of the catheter. FIGS. 20B-20F illustrate examples of the drive system of FIG. 20A in different positions relative to the patient.

As mentioned in reference to FIGS. 16A-16E, in examples of drive systems including multiple arms (e.g., robotic arms) the arms may be on different bases, which may be separately positioned relative to the patient. For example, FIGS. 21A-21E illustrates an example of an apparatus that includes a pair of bases that, similar to the example show in FIGS. 20A-20F, are positioned beneath the patient and each include a robotic arm extending up to control movement of the endoscope relative to the patient. For example, in FIG. 21A the apparatus includes a first base 2101 from which a first arm 2106 extends and a second base 2101' from which a second arm extends 2106'. The two arms may be controlled by a controller that coordinates the movements of the two arms and of any linear drive, as discussed above in reference to any of the other drive systems. In some examples one of the robotic arms may be configured to include a guide to help position the endoscope while the other arm may be coupled to the endoscope. FIGS. 21B-21E illustrate examples of the drive system of FIG. 21A in different positions relative to the patient. When not in use, the drive system may be configured to move the drive arms down and away from the region over the patient.

Figure 22:
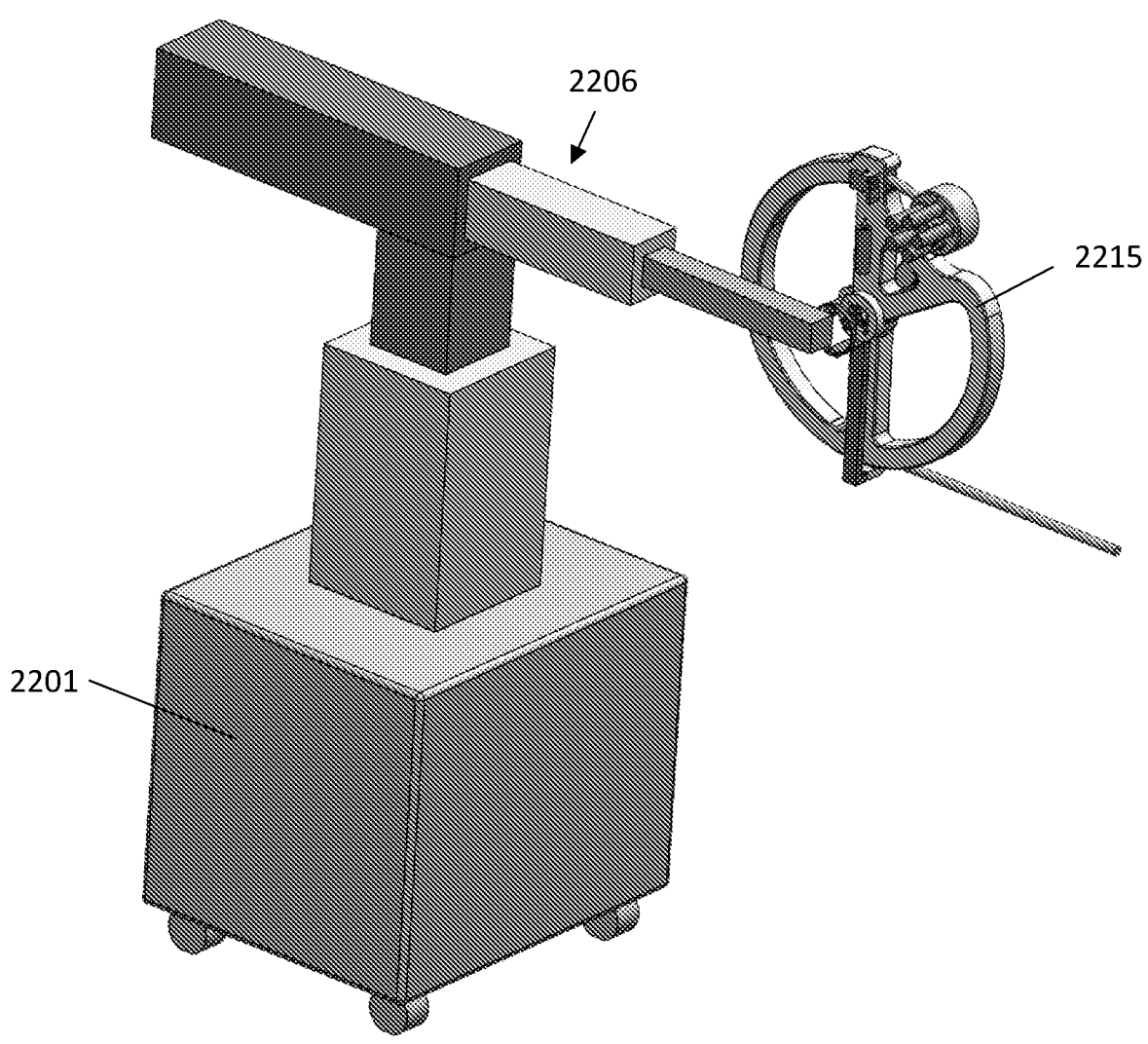
FIG. 22 schematically illustrates one example of a system for storing and dispensing a robotic scope as described herein, utilizing a robotic arm with rectilinear joints. Joints can be made that move in the vertical direction, side-to-side, and in-and-out. This example may include pan, tilt, and roll axes.

Any of the drive systems described above may be configured for use with the systems for storing and dispensing a robotic scope described in FIGS. 3-10E. For example, FIG. 22 illustrate an example of a drive system including a base 2001 and a rotatable frame 2215 that may be used to store and/or extend or retract the endoscope (e.g., a nested endoscope) as described above. The rotatable frame is coupled to the base via one or more arms 2206. In FIG. 22, the arm is a linear actuator that extends the rotatable frame proximally/distally. The configuration shown in FIG. 22 (similar to that shown in FIG. 3, above) may be positioned at the base of the patient bed, by moving the base region relative to the bed so that the rotatable frame is in line with the patient's midline and anus. The retractable/extendable arm 2206 may be withdrawn proximally or extended distally; in FIG. 22 the retractable arm may be retracted into itself while remaining sufficiently rigid so that it may support the weight and movements of the catheter (e.g., within the rotatable frame).

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for storing and dispensing a nested robotic scope comprising an inner elongate member nested with an outer elongate member, the system comprising:

a frame;

a rotation mount at a rotational center of the frame, wherein the rotation mount is configured to couple to a drive system for rotation of the frame about a rotational center;

a securement extending radially around the frame in an arc, wherein the securement is configured to hold the robotic scope;

a pivot arm coupled to an inner scope mount, wherein the inner scope mount is configured to mount to a proximal end of the inner elongate member, wherein the pivot arm is configured to rotate the inner scope mount about the rotational center to move the inner elongate member into or out of a distal end of the outer elongate member; and an exit guide configured to mount to the drive system so that the drive system rotates the frame relative to the exit guide about the rotational center, wherein rotation of the frame relative to the exit guide results in translation of the outer member of the robotic scope out of the exit guide so that the robotic scope moves linearly away from the exit guide.

2. The system of claim 1, wherein the drive system comprises a robotic arm.

3. The system of claim 1, further comprising a robotic scope mount configured to secure a proximal end of the robotic scope to the frame.

4. The system of claim 3, wherein the robotic scope mount comprises a clamp.

5. The system of claim 3, wherein the robotic scope mount is configured to couple the robotic scope to a pressure source.

6. The system of claim 1, further comprising a removable tray configured to removably mate with the securement, wherein the removable tray is configured to hold the robotic scope.

7. The system of claim 1, wherein the frame comprises a wheel.

8. The system of claim 1, further comprising a support arm coupled to the exit guide and configured to secure the exit guide to the drive system.

9. The system of claim 1, wherein the securement extends more than 180 degrees around the frame.

10. The system of claim 1, wherein the rotation mount is configured to couple the drive system to a region of the frame at a center point region of the arc formed by the securement.

11. The system of claim 1, wherein the pivot arm is configured to rotate the inner scope mount relative to the frame over an arc that is 90 degrees or less.

12. The system of claim 1, wherein the inner scope mount comprises a plurality of steering actuators configured to couple to a plurality of steering cables in the robotic scope.

13. The system of claim 1, wherein the pivot arm is configured to couple to the drive system so that the drive system drives rotation of the pivot arm about the rotational center.

14. The system of claim 1, further comprising a pressure input configured to couple the robotic scope to a pressure source to control rigidity of the robotic scope.

15. The system of claim 1, wherein the securement comprises a channel.

16. A system for storing and dispensing a nested robotic scope comprising an inner elongate member nested with an outer elongate member, the system comprising:

a frame;

a rotation mount at a rotational center of the frame, wherein the rotation mount is configured to couple to a robotic arm for rotation of the frame about a rotational center;

a securement extending radially around the frame in an arc, wherein the securement is configured to hold the outer elongate member of the robotic scope;

an exit guide;

a pivot arm coupled to an inner scope mount, wherein the inner scope mount is configured to mount to a proximal end of the inner elongate member, wherein the pivot arm is configured to rotate the inner scope mount about the rotational center to move the inner elongate member into or out of a distal end of the outer elongate member; and a support arm coupled to the exit guide and configured to secure the exit guide to the robotic arm so that the robotic arm rotates the frame about the rotational center relative to the exit guide, wherein rotation of the frame relative to the exit guide results in translation of the outer elongate member of the robotic scope out of the exit guide so that the robotic scope moves linearly away from the exit guide.

17. A system for storing and dispensing a nested robotic scope comprising an inner elongate member nested with an outer elongate member, the system comprising:

a frame;

a mount at a rotational center of the frame, wherein the mount is configured to couple to a drive system so that the drive system rotates the frame about the rotational center;

a securement extending radially around the frame in an arc, wherein the securement is configured to hold the robotic scope;

an outer robotic scope mount configured to secure a first end of the outer elongate member of the robotic scope to the frame;

a pivot arm comprising an inner scope mount, wherein the inner scope mount is configured to mount to a first end of the inner elongate member of the robotic scope, wherein the pivot arm is configured to rotate the inner scope mount about the rotational center to move the inner elongate member into or out of a second end of the outer elongate member of the robotic scope;

an exit guide configured to mount to the drive system so that the drive system rotates the frame relative to the exit guide, wherein rotation of the frame relative to the exit guide linearly translates the outer elongate member of the robotic scope out of the exit guide so that the robotic scope moves linearly away from the exit guide.

18. The system of claim 17, wherein the pivot arm is configured to rotate the inner scope mount relative to the frame over an arc that is 90 degrees or less.

19. The system of claim 17, wherein the inner scope mount comprises a plurality of steering actuators configured to couple to a plurality of steering cables in the robotic scope.

20. The system of claim 17, wherein the pivot arm is configured to couple to the drive system so that the drive system drives rotation of the pivot arm about the rotational center.

21. The system of claim 17, wherein the drive system comprises a robotic arm.

22. The system of claim 17, wherein the outer robotic scope mount comprises a clamp.

23. The system of claim 17, further comprising a removable tray configured to removably mate with the securement, wherein the removable tray is configured to hold the robotic scope.

24. The system of claim 17, wherein the frame comprises a wheel.

25. The system of claim 17, further comprising a support arm coupled to the exit guide and configured to secure the exit guide to the drive system.

26. The system of claim 17, wherein the securement extends more than 180 degrees around the frame.

27. The system of claim 17, further comprising a first pressure input configured to couple the inner elongate member to a first pressure source to control rigidity of the inner elongate member and a second pressure input configured to couple the outer elongate member to a second pressure source to control rigidity of the outer elongate member.

28. A system for storing and dispensing a nested robotic scope comprising an inner elongate member nested with an outer elongate member, the system comprising:

a frame;

a mount at a rotational center of the frame, wherein the mount is configured to couple to a robotic arm so that the robotic arm rotates the frame about the rotational center;

a securement extending radially around the frame in an arc, wherein the securement is configured to hold the robotic scope;

an outer robotic scope mount configured to secure a first end of the outer elongate member of the robotic scope to the frame;

an inner scope mount, wherein the inner scope mount is configured to mount to a first end of the inner elongate member of the robotic scope, wherein the inner scope mount is configured to move the inner elongate member into or out of a second end of the outer elongate member of the robotic scope so that the inner elongate member may move relative to the outer elongate member;

an exit guide configured to mount to the robotic arm so that the robotic arm rotates the frame relative to the exit guide, wherein rotation of the frame relative to the exit guide linearly translates the outer elongate member of the robotic scope out of the exit guide so that the robotic scope moves linearly away from the exit guide.

29. A system for storing and dispensing a nested robotic scope comprising an inner elongate member nested with an outer elongate member, the system comprising:

a drive system;

a frame mounted to the drive system at a rotational center of the frame so that the drive system rotates the frame about the rotational center;

a securement extending radially around the frame in an arc, wherein the securement is configured to hold the robotic scope;

an outer robotic scope mount configured to secure a first end of the outer elongate member of the robotic scope to the frame;

a pivot arm comprising an inner scope mount, wherein the inner scope mount is configured to mount to a first end of the inner elongate member of the robotic scope, wherein the pivot arm is configured to rotate the inner scope mount about the rotational center to move the inner elongate member into or out of a second end of the outer elongate member of the robotic scope independently of the outer elongate member;

an exit guide mounted to the drive system so that the drive system rotates the frame relative to the exit guide, wherein rotation of the frame relative to the exit guide linearly translates the outer elongate member of the robotic scope out of the exit guide so that the robotic scope moves linearly away from the exit guide.

* * * * *